(12) United States Patent
Kovatchev et al.

(10) Patent No.: US 6,923,763 B1
(45) Date of Patent: Aug. 2, 2005

(54) METHOD AND APPARATUS FOR PREDICTING THE RISK OF HYPOGLYCEMIA

(75) Inventors: Boris P. Kovatchev, Amherst, VA (US); J. Randall Moorman, Charlottesville, VA (US); William L. Clarke, Charlottesville, VA (US); Martin Straume, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 334 days.

(21) Appl. No.: 10/069,674

(22) PCT Filed: Aug. 21, 2000

(86) PCT No.: PCT/US00/22886

§ 371 (c)(1),
(2), (4) Date: Feb. 22, 2002

(87) PCT Pub. No.: WO01/13786

PCT Pub. Date: Mar. 1, 2001

Related U.S. Application Data

(60) Provisional application No. 60/150,243, filed on Aug. 23, 1999.

(51) Int. Cl.$^7$ .................................................. A61B 5/00
(52) U.S. Cl. ...................... 600/300; 600/365; 128/920
(58) Field of Search ................................. 600/300–301, 600/309, 316, 322, 365; 125/898, 920, 925; 706/924; 702/19; 235/375–385; 435/236; 708/131–132

(56) References Cited

U.S. PATENT DOCUMENTS

| | | | |
|---|---|---|---|
| 4,731,726 A | 3/1988 | Allen, III | |
| 5,019,974 A | 5/1991 | Beckers | |
| 5,822,715 A | 10/1998 | Worthington et al. | |
| 5,840,020 A | 11/1998 | Heinonen et al. | |

OTHER PUBLICATIONS

Kovatchev, et al., "Assessment of Risk for Severe Hypoglycemia Among Adults with IDDM," Diabetes Care, vol. 21, No. 11, pp. 1870–1875, (Nov., 1998).

Kovatchev, et al., "Modeling Insulin–Glucose Dynamics During Insulin Induced Hypoglycemia. Evaluation of Glucose Counterregulation," Journal of Theoretical Medicine, vol. 1, pp. 313–323, (Oct. 21, 1998).

Kovatchev, et al., "Dynamic network model of glucose counter–regulation in subjects with insulin–requiring diabetes," Methods in Enzymology, vol. 321, pp. 396–410: Numerical Computer Methods, Part C, 2000.

Cox, D.J., Kovatchev, B.P., Julian, D.M., Gonder–Frederick, L.A., Polonsky, W.H., Schlundt, D.G. and Clarke, W.L. (1994). Frequency of Severe Hypoglycemia in Insulin–Dependent Diabetes Mellitus can be Predicted from Self–Monitoring Blood Glucose Data. (1994). J.of Clin. Endocrinology & Metabolism, 79(6), pp. 1659–1662.

Kovatchev, B.P., Cox, D.J., Gonder–Frederick, L.A. and Clarke, W. (1997). Symmetrization of the Blood Glucose Measurement Scale and Its Applications. Diabetes Care, vol. 20, No. 11, pp. 1655–1658.

*Primary Examiner*—Max F. Hindenburg
*Assistant Examiner*—Michael Astorino
(74) *Attorney, Agent, or Firm*—Robert J. Decker

(57) ABSTRACT

The invention relates to a method which utilizes blood glucose ("BG") sampling, insulin infusion/injection records, heart rate ("HR") information and heart rate varability ("HRV") information to estimate BG in the near future and to estimate of the risk of the onset of hypoglycemia. The invention also relates to an apparatus for predicting BG levels and for assessing the risk of the onset of hypoglycemia in the near future. The invention is based on two predetermined bio-mathematical routines: a network model of BG fluctuations and a BG profile for assessment of the risk of hypoglycemia.

16 Claims, 14 Drawing Sheets

Figure 1: Major Factors Determining Blood Glucose Dynamics

Figure 2: Dynamic Network Model of BG Fluctuations

Figure 6: The Distribution of the Transformed BG Readings

Figure 7 : Defining the BG Risk Function

Figure 9: Risk Groups Identified by the Low BG Index and Number of Future SH Episodes Hyperinsulinemic Clamp: Design of the Study

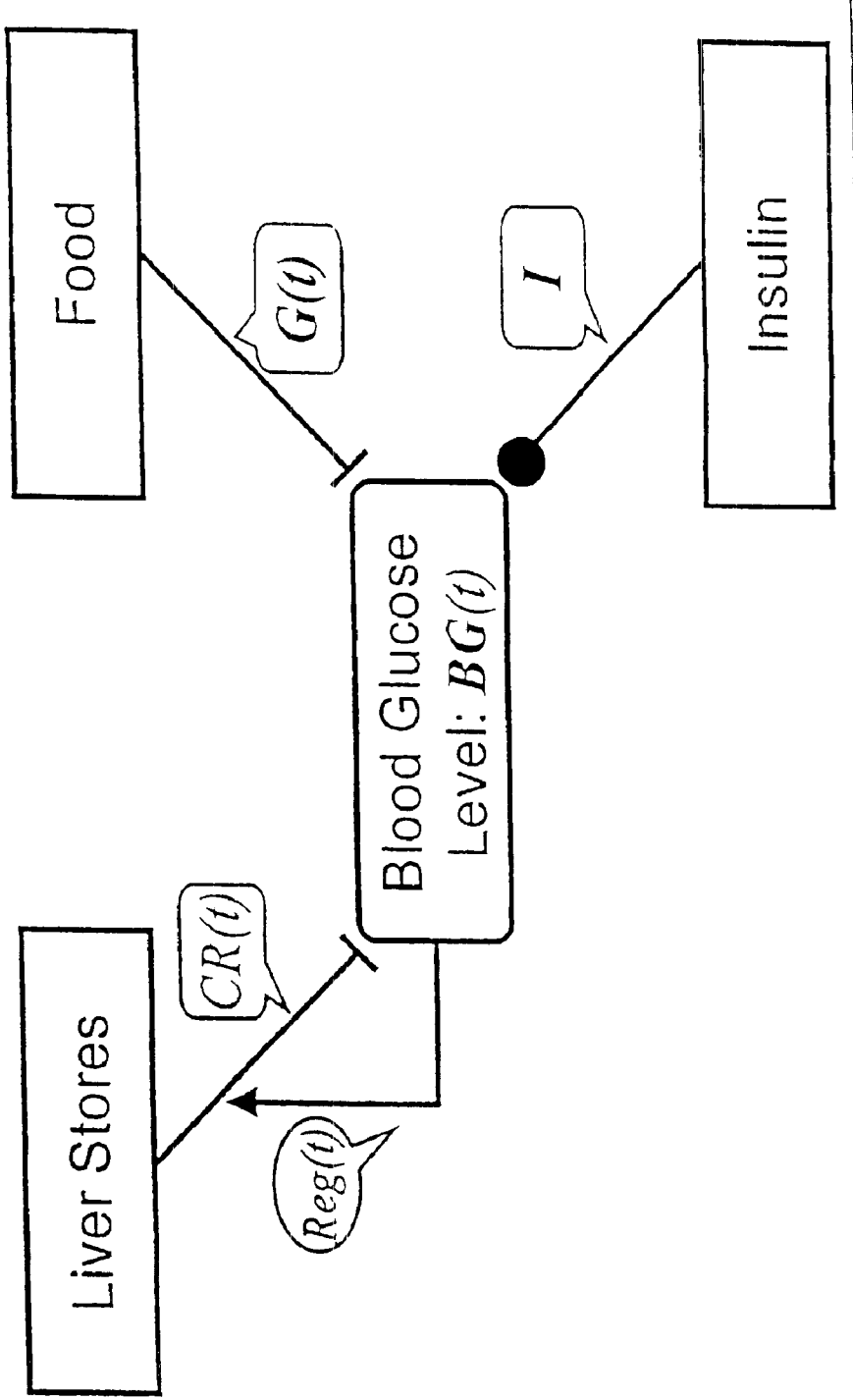
Figure 11: Insulin-Glucose-Counterregulation Network During Controlled Hyperinsulinemic Clamp

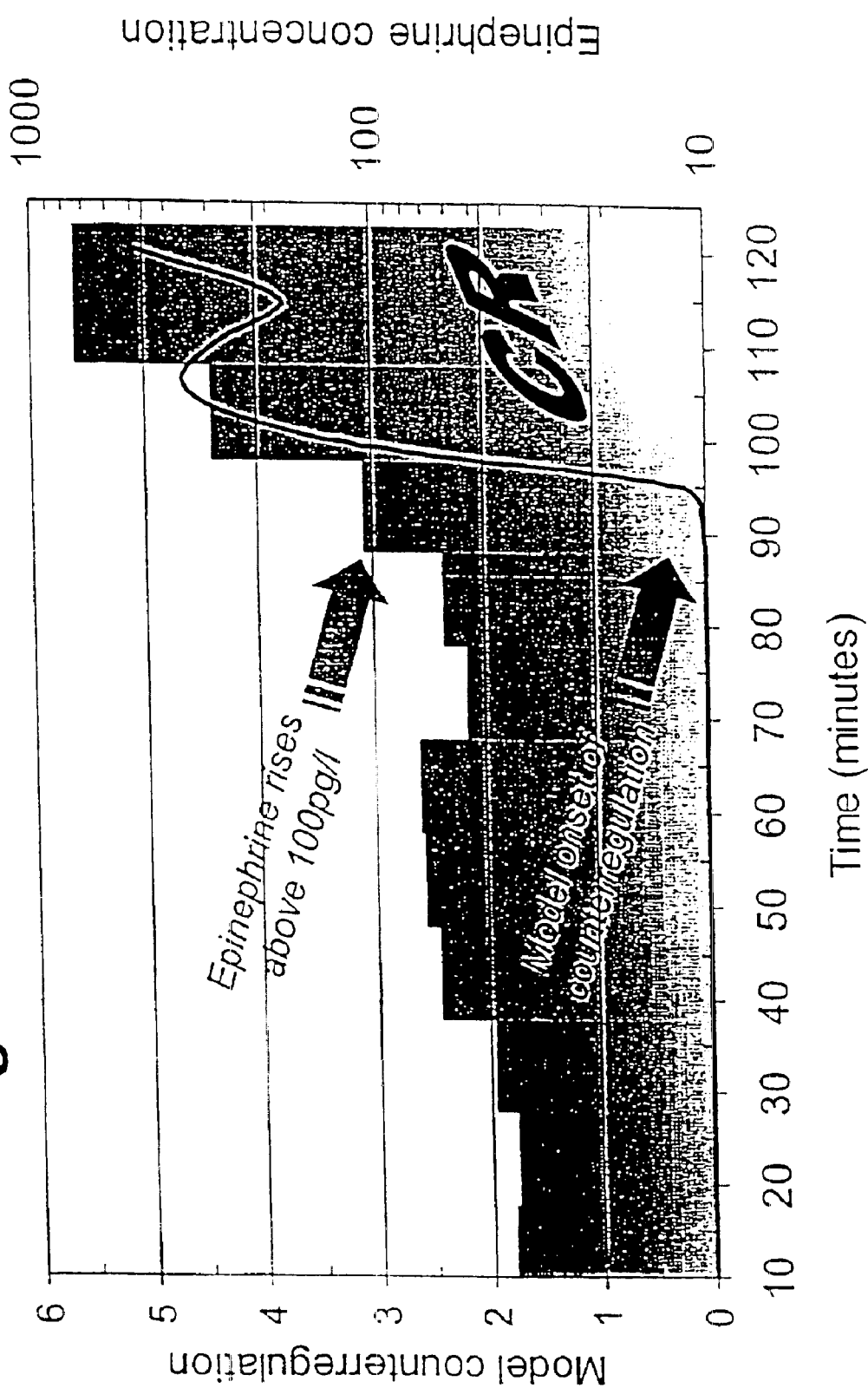
Figure 12. Counterregulation

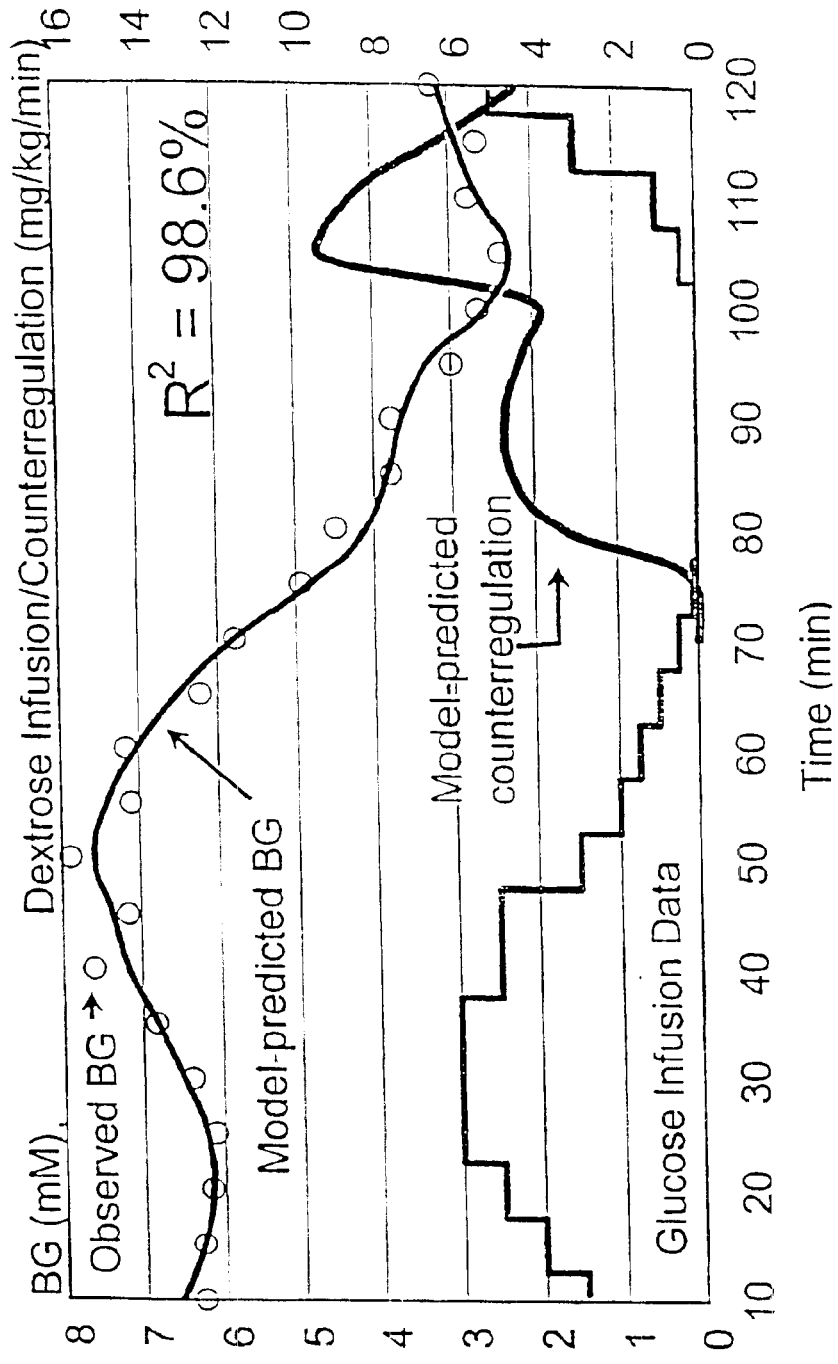

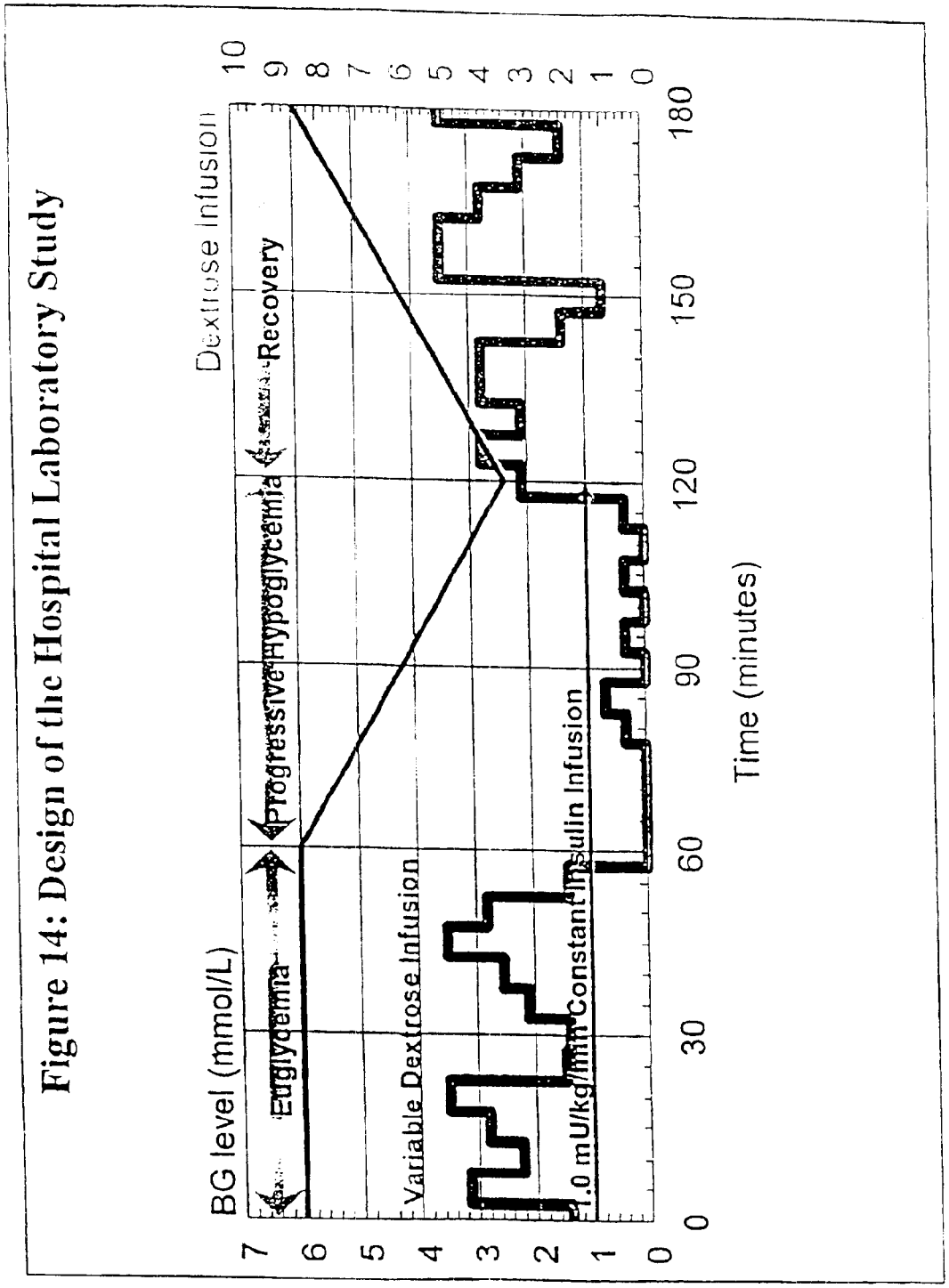
Figure 14: Design of the Hospital Laboratory Study

METHOD AND APPARATUS FOR PREDICTING THE RISK OF HYPOGLYCEMIA

This application claims the benefit of Provisional Appl. 60/150,243, filed Aug. 23, 1999.

TECHNICAL FIELD

The invention relates to a method and apparatus for monitoring and predicting near future blood glucose levels and for estimating the risk of the onset of hypoglycemia in patients with Insulin Dependent Diabetes.

BACKGROUND ART

In a healthy person, the blood glucose ("BG") level is internally regulated through insulin released from the pancreas that counterbalances carbohydrate intakes from food, drinks, etc. Because patients with Type 1 Diabetes Mellitus ("T1DM") are unable to produce sufficient amounts of insulin, this internal self-regulation is disrupted. The standard daily control of T1 DM involves multiple insulin injections, or a continuous insulin infusion using an insulin pump, that lowers BG. However, this external BG control is not nearly as precise or reliable as the internal self-regulation, e.g., too little insulin results in chronic high BG levels, too much can cause hypoglycemia.

Extensive recent studies have demonstrated that the most effective long-term control of T1DM results from the strict maintenance of BG levels within a normal range through intensive insulin therapy. Detailed results were presented by the 10-year Diabetes Control and Complications Trial ("DCCT") and its European counterpart. See The Diabetes Control and Complications Trial Research Group, "The effect of intensive treatment of diabetes on the development and progression of long-term complications of insulin-dependent diabetes mellitus," NEJM, 329: 978–86 (1993); Reichard P, et al., "Mortality and treatment side-effects during long-term intensified conventional insulin treatment in the Stockholm Diabetes Intervention study," Diabetes, 43: 313–17 (1994).

The DCCT proved that chronic high BG levels cause many complications in multiple body systems over time, while too much insulin results in hypoglycemia. Without immediate treatment, hypoglycemia can rapidly progress to severe hypoglycemia ("SH"), a condition identified by low BG resulting in stupor, seizure or unconsciousness that precludes self-treatment. If the patient does not receive treatment during an SH episode, death can occur. Approximately 4% of deaths in T1DM patients are attributed to SH. In short, while on one hand, intensive therapy is the best long-term treatment of T1DM, on the other it has been associated with at least a threefold increase in SH.

Since SH can result in accidents, coma and even death, it discourages patients and health care providers from pursuing intensive therapy. Consequently, hypoglycemia has been identified as a major barrier to improved glycemic control. See Cryer P E, "Hypoglycemia begets hypoglycemia," Diabetes, 42: 1691–93 (1993); Cryer P E, et al., "Hypoglycemia" Diabetes Care 17: 734–55 (1994). In other words, patients with T1DM face a life-long clinical optimization problem, i.e., to maintain strict glycemic control without increasing risk for hypoglycemia. A bio-mathematical problem associated with this optimization is to create a quantitative procedure that would continuously assess the risk of hypoglycemia, thus providing means for external regulation of BG within optimal limits.

A significant problem with such an approach is the detection of hypoglycemia prior to the development of neurogenic symptoms. Numerous studies have investigated the occurrence of hypoglycemia-related symptoms and generally found that such warning signs occur and are recognized by patients in less than 50% of all hypoglycemic episodes and are associated with quite low BG levels of 70 mg/dl and below. See Boyle P J, et al., "Plasma glucose concentrations at the onset of hypoglycemic symptoms in patients with poorly-controlled diabetes and in nondiabetics," NEJM, 318: 1487–92 (1988); Clarke W L, et al., "Multifactorial origin of hypoglycemic symptoms unawareness in IDDM: Association with defective glucose counterregulation and better glycemic control," Diabetes. 40: 680–85 (1991); Clarke W L, et al., "Reduced awareness of hypoglycemia in IDDM adults: A prospective study of hypoglycemia frequency and associated symptoms," Diabetes Care, 18: 517–22 (1995); Cox D J, et al., "Perceived symptoms in the recognition of hypoglycemia," Diabetes Care, 16: 519–27 (1993); Cox D J, et al., "Sex differences in BG thresholds for counterregulatory hormone release and low blood glucose symptom perception," Diabetes Care, 19: 269–70 (1996).

This means that about half of all hypoglycemic episodes are asymptomatic, or unrecognized, and even if recognized in many cases represent dangerously low BG levels. Reliable automated recognition of upcoming hypoglycemia would allow for intensified insulin therapy with reduced fear of hypoglycemia. The benefit of such a strategy includes reduced damage to eyes, nerves, kidneys and blood vessels of diabetics, lower health care costs and reduced morbidity and mortality in T1DM cases.

Efforts to predict hypoglycemia have not been effective in the past, and attempts to predict a patient's vulnerability to SH have been particularly unsuccessful. Various approaches to assess the risk of SH have been tested, including low $HbA_{1c}$, intensive therapy, inadequate hormonal counter-regulation, hypoglycemia unawareness, and a history of SH. For instance, the DCCT (with intensive therapy) demonstrated that only about 8% of future SH could be predicted from known variables. See "The DCCT Research Group: Epidemiology of severe hypoglycemia in the diabetes control and complications trial," Am. J. Med, 90: 450–59 (1991).

A recent structural equation model accounted for 18% of the variance of SH using history of SH, hypoglycemia awareness and autonomic score. See Gold A E, et al, "A structural equation model for predictors of severe hypoglycemia inpatients with insulin-dependent diabetes mellitus," Diabetic Med., 14: 309–15 (1997).

Another mathematical model was developed taking the patient's diet, medication and physical strain into account to provide predictive blood glucose values. See U.S. Pat. No. 5,840,020 to Heinonen, et al. A diabetes management system for predicting future blood glucose concentrations based upon current blood glucose concentrations and the insulin action remaining from previous insulin doses has also been proposed. See U.S. Pat. No. 5,822,715 to Worthington, et al.

However, none of these models accurately predict the risk of SH or the onset of hypoglycemia.

SUMMARY OF THE INVENTION

The present invention relates to a method which utilizes BG sampling, insulin infusion/injection records, heart rate ("HR") information and heart rate variability ("HRV") information to predict BG levels and the onset of hypoglycemia in the near future based on an assessed risk of hypoglycemia. The invention also relates to an apparatus for predicting BG levels and the onset of hypoglycemia. Another aspect of the invention relates to a method and apparatus for assessing the risk of hypoglycemia on the basis of BG measurements. The invention is based on two predetermined bio-mathematical routines: a network model of BG fluctuations and a BG profile for assessment of the risk of hypoglycemia.

In one aspect of the invention, a method for predicting a near future BG profile and the onset of hypoglycemia is provided which generally includes the steps of 1) monitoring and recording a BG history profile; 2) monitoring and recording an insulin infusion/injection history profile; 3) monitoring and recording a HR history profile as an estimate of physical activity, 4) monitoring and recording a HRV history profile as an estimate of sympathetic nervous system activity; 5) processing the recorded BG insulin infusion/ injection. HR, and HRV history profiles using a first predetermined bio-mathematical routine to predict a near future BG profile; and 6) evaluating the near future BG profile to predict the onset of hypoglycemia in the near future based on an assessed risk of hypoglycemia, wherein the assessed risk of hypoglycemia is determined using a second predetermined bio-mathematical routine.

In another aspect of the invention, the method includes the steps of 1) receiving data input regarding BG history, insulin infusion/injection history, HR history, and HRV history; 2) processing the data received using a first predetermined bio-mathematical routine to predict a near future BG profile; and 3) evaluating the near future BG profile to predict the onset of hypoglycemia in the near future based on an assessed risk of hypoglycemia, wherein the assessed risk of hypoglycemia is determined using a second predetermined bio-mathematical routine.

According to another aspect of the invention, an apparatus is provided which generally includes: 1) a BG history profile recording mechanism; 2) an insulin infusion/injection history profile recording mechanism; 3) a HR history profile recording mechanism; 4) a HRV history profile recording mechanism; 5) a near future BG profile prediction module which operates using a first predetermined bio-mathematical routine; and 6) a hypoglycemia prediction module which operates based on an assessed risk of hypoglycemia, wherein the assessed risk of hypoglycemia is determined using a second predetermined bio-mathematical routine.

Another aspect of this invention is directed to an apparatus which includes: 1) an interface for receiving data regarding a BG history profile, an insulin infusion/injection history profile, a HR history profile, and a HRV history profile; 2) a BG prediction module for predicting a near future BG profile using a first predetermined bio-mathematical routine; and 4) a hypoglycemia prediction module for predicting the onset of hypoglycemia in the near future based on an assessed risk of hypoglycemia, wherein the assessed risk of hypoglycemia is determined using a second predetermined bio-mathematical routine.

In yet another aspect of the invention, a method and apparatus for assessing the risk of hypoglycemia are provided which involve assessing the risk of hypoglycemia based on a determined Low BG Index.

A method for assessing the risk of hypoglycemia based on a Low BG Index according to the present invention includes the steps of: 1) receiving and recording a BG history profile; 2) transforming the BG history profile scale to obtain a symmetrical distribution scale; 3) introducing a BG Risk Function to obtain a Low BG Index; and 4) determining the risk of hypoglycemia based on the Low BG Index.

A system or apparatus for assessing the risk of hypoglycemia based on a Low BG Index is also provided which includes 1) an interface for receiving a BG history profile; 2) a BG history profile scale transformation module for transforming the BG history profile scale into a symmetrical distribution scale; 3) a BG Risk Function module for obtaining a Low BG Index; and 4) a hypoglycemia risk classification module for determining the assessed risk of hypoglycemia based on the Low BG Index. Again, the interface for receiving the BG history profile can be configured to either accept manual input regarding the BG history profile, or it can be configured as an automated data acquisition unit coupled with a BG monitoring device.

These and other features and advantages of the present invention will become apparent from the following disclosure of the invention with reference to the description and Figures herein.

DISCLOSURE OF THE INVENTION

The invention has many advantages, one being that until now there has existed no method or apparatus for accurately predicting BG profiles in the near future. Generally, the term "near future" means within approximately one to two hours from the time of prediction or assessment. As a result, T1DM patients are biased to tolerating high BG levels in order to avoid the uncomfortable and sometimes dangerous situation of hypoglycemia. Among other things, the invention allows for better glycemic control in individuals with T1DM, thus reducing severe complications of damage to eyes, nerves, kidneys, blood vessels and heart muscle. For example, the invention can be incorporated into an "intelligent" insulin pump which is programmed to optimize insulin infusion rates based on the predicted near future BG profile and the estimated risk of hypoglycemia.

In accordance with the invention, a method for the predicting a near future BG profile and predicting the onset of hypoglycemia in the near future is provided which utilizes information regarding: 1) BG history; 2) insulin infusion/ injection history; 3) estimates of preceding physical activity from HR history, and 4) estimates of sympathetic nervous system activity from HRV history: to predict a near future BG profile. The predicted near future BG profile can then be used to predict the onset of hypoglycemia based on an assessment of the risk of hypoglycemia. While not wishing to be limited by theory, it is believed that these physiological measurements serve as BG predictive factors as discussed below.

More particularly, a method according to the invention can include the steps of 1) receiving input data regarding BG history profiles, insulin injection/infusion history profiles; HR history profiles; and HRV history profiles; 2) processing the input data using a first predetermined bio-mathematical routine to predict a near future BG profile; and 3) evaluating the near future BG profile to predict the onset of hypoglycemia in the near future based on an assessed risk of hypoglycemia, wherein the assessed risk of hypoglycemia is determined using a second predetermined bio-mathematical routine. The input data can either be received by manual input from an external source, such as a patient or medical care giver, or by automated data acquisition from a monitoring device or mechanism.

In another aspect of the invention, a method for predicting a near future BG profile and for predicting the onset of hypoglycemia is provided which includes the steps of 1) monitoring and recording a BG history profile; 2) monitoring and recording an insulin infusion/injection history profile; 3) monitoring and recording a HR history profile; 4) monitoring and recording a HRV history profile; 5) evaluating the recorded BG, insulin infusion/injection, HR and HRV history profiles using a first predetermined bio-mathematical routine to predict a near future BG profile; and 6) evaluating the near future BG profile to predict the onset of hypoglycemia in the near future based on an assessed risk of hypoglycemia, wherein the assessed risk of hypoglycemia is determined using a second predetermined bio-mathematical routine.

A method according to the invention can further include the step of adjusting the insulin infusion/injection rate based on the predicted near future BG profile and the predicted onset of hypoglycemia.

In yet another aspect of the invention, a system or apparatus for predicting near future BG profiles and predicting the onset hypoglycemia is provided. A system or apparatus according to the invention can include 1) a BG history profile recording mechanism; 2) an insulin infusion/injection history profile recording mechanism; 3) a HR history profile recording mechanism; 4) a HRV history profile recording mechanism; 5) a near future BG profile prediction module which operates using a fist predetermined bio-mathematical routine; and 6) a hypoglycemia prediction module which operates based on an assessed risk of hypoglycemia, wherein the assessed risk of hypoglycemia is determined using a second predetermined bio-mathematical routine.

In one embodiment of the invention, a system or apparatus can incorporate another device, such as a BG monitoring device or insulin pump. For example, an apparatus of the invention can be configured as a portable device which includes 1) an interface for receiving data input regarding a BG history profile, an insulin infusion/injection history profile, a HR history profile, and a HRV history profile; 2) a near future BG profile prediction module for predicting a near future BG profile using a first predetermined bio-mathematical routine; and 4) a hypoglycemia prediction module for predicting the onset of hypoglycemia in the near future based on an assessed risk of hypoglycemia, wherein the assessed risk of hypoglycemia is determined using a second predetermined bio-mathematical routine. The portable device can be configured in any manner known in the art, such as but not limited to, a wristwatch-type device or a hand-held calculator-type device.

Alternatively, a system or apparatus of the invention can be incorporated into an insulin infusion pump which includes an interface for receiving data input regarding a BG history profile; a HR and HRV detection module; a near future BG profile prediction module; a hypoglycemia onset prediction module; and an insulin regulation module. According to this embodiment of the invention, the insulin regulation module can be configured to adjust insulin infusion rates based on the predicted near future BG profile and the predicted onset hypoglycemia. For instance, insulin infusion rates can be reduced if the onset of hypoglycemia is predicted.

Another implementation of the invention is embodied in a stand-alone system or apparatus for the prediction of near future BG profiles and the onset of hypoglycemia Such a device may be comprised of: 1) A BG monitoring unit for measurement and recording of a BG history profile; 2) an insulin infusion unit or insulin pump for providing insulin and recording an insulin history profile; 3) an EKG recorder for determining and recording HR and HRV history profiles, 4) a BG prediction module for predicting near future BG profiles using a first predetermined bio-mathematical routine; and 5) a hypoglycemia prediction module for predicting the onset of hypoglycemia in the near future based on an assessed risk of hypoglycemia, wherein the assessed risk of hypoglycemia is determined using a second predetermined bio-mathematical routine. The device may contain a mechanism by which it will warn the individual of the onset of hypoglycemia. Alternatively, it may contain an "intelligent" self-adjusting insulin pump with implantable or subcutaneous components which can adjust the delivering of insulin based on the predicted near future BG profile and the assessment of the risk of hypoglycemia.

In yet another aspect of the invention, a hypoglycemia risk assessment module is provided which can either be a separate device, independent of the system or apparatus for predicting a near future BG profile and the onset of hypoglycemia, or alternatively can be incorporated into the system or apparatus as an additional component or module. The hypoglycemia risk assessment module can include 1) an interface for receiving a BG history profile; 2) a BG history profile scale transformation module for transforming the BG history profile scale into a symmetrical distribution scale; 3) a BG Risk Function module for obtaining a Low BG Index; and 4) a risk classification module for determining the assessed risk of hypoglycemia based on the Low BG Index.

In this regard, the invention is also drawn to a method for assessing the risk of hypoglycemia based on a Low BG Index including the steps of 1) receiving and recording a BG history profile; 2) transforming the BG history profile scale to obtain a symmetrical distribution scale; 3) introducing a BG Risk Function to obtain a Low BG Index; and 4) determining the risk of hypoglycemia based on the Low BG Index.

The above descriptions are exemplary embodiments of the invention. It is understood that various combinations and modifications of the embodiments will be apparent to one of skill in the art. For instance, the method and apparatus according to the invention can incorporate any combination or subcombination of BG-regulating physiological parameter monitoring devices, or may merely include an interface for receiving externally generated data regarding the BG-regulating physiological parameters.

Further, a method or apparatus according to the invention can incorporate an on-line assessment of the risk of hypoglycemia based on the BG history profiles received to automatically update hypoglycemia risk assessments and thus predictions of the onset of hypoglycemia. Alternatively, the risk of hypoglycemia can be assessed off-line by a standalone risk assessment module and incorporated into a method or apparatus of the invention as a programmed parameter.

Physiological Considerations and Modeling:

As illustrated in FIG. 1, BG dynamics in individuals with T1DM is a continuous process dependent on the temporal patterning of at least three external behavioral factors: food intake, insulin injection/infusion and physical activity, and on internal physiologic factors such as hormonal counter-regulation. Food intake elevates BG, while insulin and physical activity depress BG levels. Sometimes, a sufficiently low BG level triggers a physiologic reaction to hypoglycemia, identified as hormonal counter-regulation.

The invention builds on findings presented in two publications by the present inventors: Kovatchev, et al., "Modeling insulin-glucose dynamics during insulin induced hypoglycemia: Evaluation of glucose counter-regulation," *J. of Theoretical Medicine* 1: 313–23 (1999) and Kovatchev, et al., "Assessment of risk for severe hypoglycemia among adults with IDDM: Validation of the Low Blood Glucose Index," *Diabetes Care* 21: 1870–75 (1998), both of which are herein incorporated by reference in a manner consistent with this disclosure.

In addition to these findings, the invention utilizes estimates of the degree to which counter-regulatory mechanisms are activated and evaluation of prior physical activity based on measurements of HR and HRV. Without intending to be limited by theory, it is believed that these factors are reflective of counter-regulatory mechanisms because the predominant mechanism by which the body responds to hypoglycemia is activation of the sympathetic nervous system. The sympathetic neurohormones epinephrine and norepinephrine oppose insulin action and lead to a diminished rate of fall of BG. The invention also incorporates the concept that the degree of sympathetic nervous system activation can be estimated from HRV, while the overall preceding physical activity can be evaluated from average HR.

FIG. 2 presents the general scheme of BG dynamics as a function of three principal temporal behavioral variables known to exert regulatory control on BG level: $P_1(t)$—food intake, $P_2(t)$—insulin injection/infusion, and $P_3(t)$—physical activity, as well as one principal temporal physiological variable, $CR(t)$—a counter-regulatory process through which available liver stores replenish low BG levels. Thus, the system is defined in terms of five time dependent state variables: 1) BG level, 2) food intake, 3) insulin injection/infusion, 4) physical activity and 5) liver stores for replenishing low BG levels.

This network of processes provides the functional regulatory interactions responsible for BG control. BG levels will be positively affected by food intake (process $P_1$), as well as by the potential for replenishment when BG is low from available liver stores (process CR). The negative effect on BG level by insulin is denoted by process $P_2$, whereas the reduction in BG brought about by physical activity is referred to by process $P_3$.

The counter-regulatory loop between liver stores and BG is implemented by way of 1) inhibition of process CR by elevated BG levels (process Reg) (i.e., a release from inhibition of process CR below some threshold BG level, thus providing for counter-regulatory recovery from low BG levels by recruitment of available liver stores), and 2) replenishment of liver stores under conditions during which BG levels are not low (by process Rep). One additional regulatory interaction (process RI) makes reference to the physical activity-based enhancement of insulin's effectiveness in down-regulating BG via $P_2$.

Bio-Mathematical Routine for the Prediction of Near Future BG Profiles:

As described above, the BG level at any future point in time depends on the following physiological parameters: 1) current BG level (which indicates previous food intake as well); 2) ongoing insulin infusion; 3) past and current physical activity as evaluated from HR; and 4) hormonal counter-regulation as estimated from indicators of autonomic nervous system activity evaluated from HRV.

The four BG-regulating factors will be measured, or indirectly assessed, on relatively regular time intervals. A "profile" of the BG-regulating factors according to the invention can include a compilation of at least two measurement. For instance, an average interval between two consecutive BG determinations to generate a BG history profile can range from about 0.5 to 3 hours, and is preferably about one hour.

The mathematical problem then is, using this network of interactions, to determine BG at moment (t) using BG, insulin, physical activity, and counter-regulation assessments at a previous moment (t−1). According to the invention, it has been discovered that a functional form for the BG rate of change may be given by the following non-linear differential equation:

$$\frac{dBG(t)}{dt} = -PA(HR(t-1, t-k)) - \frac{aBG(t)}{\varepsilon + BG(t)^2} I(t-1, t-k) + CR(HRV(t-1))$$

Where it is assumed that:
1) The BG rate of change is affected positively by the function BG(t−1,t−k), a composite representation of previous BG readings, and by the function CR(HRV(t−1)), a representation of counter-regulatory response through HRV.
2) The BG rate of change is affected negatively by the insulin infusion at a previous moment l(t−1) and the insulin effectiveness is inversely affected by the BG level at time (t) that is to be determined by parameter "a". The latter is incorporated in the equation by the non-linear term $$\frac{aBG(t)}{\varepsilon + BG(t)^2}.$$

3) The BG elimination is accelerated by preceding physical activity, represented by the cumulative action PA(HR(t−1,t−k)) of previous HR readings.

The bio-mathematical routine for predicting a near future BG profile described above can be implemented on any conventional processor known in the art which is capable of processing the predetermined bio-mathematical routine to calculate the predicted near future BG profile. All analyses can be performed in an on-line manner by automated custom developed program implementations capable of intelligent, history-based decision-making.

For instance, in one embodiment of the invention the predetermined bio-mathematical routine can be analyzed using a modified Gauss-Newton nonlinear least squares parameter estimation algorithm (See Johnson & Frasier, "Nonlinear least squares analysis," *Methods in Enzymology* 117: 301–42 (1985); Straume, et al., "Least-squares analysis of fluorescence dam" *Topics in Fluorescence Spectroscopy, Volume 2: Principles* (ed., J R Lakowicz), New York: Plenum: 177–241 (1991)) in which the differential equations characteristic of the model can be integrated numerically for BG(t) by a fourth-fifth order Runge-Kutta method (See Press, et al. "Numerical Recipes in FORTRAN," *The Art of Scientific Computing*, Cambridge University Press, New York (1994)). This model can explicitly quantify individual subjects' dextrose utilization and insulin sensitivity, as well as their counter-regulatory threshold, velocity, and capacity.

Field study dynamic for casts of future BG levels, in terms of risk function assessments, can be similarly performed, by dynamically estimating parameter values characteristic of each subject's individual process functions. Specifically, explicitly-defined parameters can be estimated to quantify the effects of (i) physical activity history (PA(t−1,t−k) from heart rate data, HR(t)); (ii) insulin infusion history (l(t−1) from information recorded by subjects' insulin pumps); (iii) current insulin sensitivity (the parameter $\alpha(t)$); (iv) prior blood glucose history (BG(t−1,t−k) as a surrogate for subjects' food intake history); and (v) counter-regulatory history (CR(t−1) from estimates of heart rate variability, HRV (t)) (FIG. 3).

The parameters of the model, insulin and glucose sensitivity, can be iterated and individually adjusted by long-term application of the predetermined biomathematical routine described above. This routine predicts the expected lower bound for the BG level at time (t) since it ignores unpredictable factors such as self-treatment behaviors prompted by occurrence of hypoglycemic symptoms. In other words, the model evaluates how low the BG can go at time (t) if the patient does not detect by symptoms, or does not treat with carbohydrates, upcoming hypoglycemia. Following a prediction of upcoming hypoglycemia, a warning to the patient to prevent its occurrence can be issued. Further, in one embodiment of the invention, an apparatus according to the invention can include a programmable insulin pump which can automatically reduce the insulin infusion rate until euglycemia is achieved.

The prediction of the onset of hypoglycemia based on the predicted near future BG profile can be accomplished by comparing the lower bound of the predicted profile to the lower bound of a BG target range. The BG target range can be set through an assessment of a patient's long-term vulnerability to hypoglycemia as described below.

Bio-Mathematical Routine for Assessment of the Risk of Hypoglycemia:

The patient's long-term vulnerability to hypoglycemia can be evaluated using a BG Risk Function based on a transformation of the BG measurement scale as described below. In essence, given numerous estimates of a patients' lower BG bounds over time, an assessment of this patient's risk for future SH can be made by computing his/her Low BG Index. The accuracy of the Low BG Index as a predictor of SH is demonstrated below. If high long-term risk for hypoglycemia is assessed, the permissible lower bound of the BG target range for the patient can be raised as a safety precaution.

Risk Analysis of Blood Glucose Data: Defining the Low BG Index:

Based on a marker of the risk of future SH centered on self-monitoring of BG data, a mathematical model, BG scale transformation, and a statistical procedure for risk analysis of BG data was developed according to the invention. Most importantly, it has been discovered that the Low BG Index is a powerful on-line predictor of SH. The idea for creating this new quantitative approach to evaluation of the risk of hypoglycemia was prompted by the historically unsuccessful prediction of SH (only about 8% of the variance accounted for) in the DCCT and other studies that used traditional predictors, such as $HbA_{1c}$, history of SH, hypoglycemia awareness, etc.

It has been determined that the basis for the previous poor prediction was mathematical, rather than clinical, in that it lies in the fact that the BG measurement scale is substantially asymmetric. The typical distribution of BG readings of a person with T1DM is usually substantially skewed. In other words, the "numerical center" of the data is substantially separated from its "clinical center." Thus, clinical conclusions, based on numerical methods, are less accurate for the constricted hypoglycemic range.

According to the invention, a data transformation is provided that symmetrizes the BG scale around a single numerical/clinical center of about 6.25 mmol/L, converts a typical distribution of BG readings into a normal distribution, and establishes a mathematical background for risk analysis of BG data through introduction of the BG Risk Function.

It has been discovered that the BG measurement scale can be symmetrized as follows. The whole range of most BG reference meters is from about 1.1 to about 33.3 mmol/L, which is considered to cover substantially all clinically observed values. The target BG range for a person with T1DM is generally considered to be about 3.9 to about 10 mmol/L. Hypoglycemia is usually identified as a BG below about 3.9 mmol/L, while hyperglycemia is a BG above about 10 mmol/L. It is obvious that this scale is not symmetric— the hyperglycemic range (10 to 33.3 mmol/L) is much greater than the hypoglycemic range (1.1–3.9 mmol/L), and the euglycemic range (3.9–10 mmol/L) is not centered within the scale. As a result, the numerical center of the scale (17.2 mmol/L) is distant from its "clinical center"—the clinically desired clustering of BG values of patients with diabetes around about 6.0–6.5 mmol/L.

FIG. 4 presents the effect of this asymmetry by way of a typical BG data distribution of 186 readings downloaded from a memory meter. The distribution is substantially skewed and the superimposed normal density poorly describes the data. In order to correct this problem, the BG scale is transformed, based on two clinical assumptions: 1) the whole transformed BG range is symmetric about 0, and 2) the target transformed BG range is symmetric about 0. These assumptions lead to a system of nonlinear equations that, when solved numerically, yield the data transformation presented by the thick gray line in FIG. 5. After the transformation, both the clinical and the numerical center of the scale coincide with zero, and the euglycemic range becomes symmetric about zero. As a result, the distribution of BG readings of a subject with T1DM becomes symmetric, or is statistically "normalized" (FIG. 6).

Once the BG scale is symmetrized, a risk analysis of BG data can be performed through introduction of a BG Risk Function. For example, the BG Risk Function can be a quadratic function such as:

$$\text{Risk}(BG) = 10 * (\text{Transformed}(BG))^2$$

Introducing such a BG Risk Function provides an "equal weighting" of both hypo- and hyperglycemic ranges of the BG scale (FIG. 7). Therefore, statistical procedures based on the symmetrized BG scale will be equally sensitive to hypoglycemic and to hyperglycemic readings. The Low BG Index can be computed as the mean of the risk values across the BG history profile. The Low BG Index can then serve as the basis for assessing the risk of hypoglycemia, i.e., the higher the Low BG Index, the higher the risk of hypoglycemia.

More particularly, the Low BG Index provides means for classification of the subjects with regard to their risk for SH. For example, on the basis of one-month of routine SMBG readings, it was found that subjects with a Low BG Index below 2.5 (low risk group) experienced, on average, 0.4 SH episodes within the following 6 months whereas subjects at a moderate risk (Low BG Index between 2.5 and 5) experienced 2.3 SH episodes in the following 6 months, while subjects at high risk (Low BG Index above 5) experienced 5.2 SH episodes in the following 6 months (FIG. 9). Based on these findings, it appears that the Low BG Index is a relatively accurate predictor of the risk of hypoglycemia based on self-monitoring BG data.

Given numerous estimates of a patients' lower BG bounds over time, an assessment of the patient's risk for future SH can be made by computing his/her own Low BG Index. Based on the computed Low BG Index, if high long-term risk for hypoglycemia is assessed, the permissible lower BG bound for the patient can be raised as a safety precaution.

For instance, once the BG Risk Function is introduced in the transformed BG scale, the BG scale can be converted to the original BG scale to establish a BG target range (FIG. 8). The BG target range can then serve as a predictor of the onset of hypoglycemia in the near future. That is, the predicted near future BG profile can be compared to the lower bound of the BG target range to predict the onset of hypoglycemia in the near future. Further, if the Low BG Index is high, and thus the assessed risk of hypoglycemia is highs the lower bound of the BG target range can be adjusted to a higher value. In this regard, the onset of hypoglycemia in the near future will be predicted based on a near future BG profile with a relatively higher lower bound BG level.

The Low BG Index as a predictor of SH was validated by a large data set containing about 13,000 SMBG readings for 96 adults with T1DM. These subjects had an average age of 35±8 yrs., a duration of diabetes of 16±10 yrs., and an $HbA_{1c}$ of 8.6±1.8%. Forty-three subjects had a recent history of SH, while 53 did not. All subjects used Lifescan One Touch II meters to collect an average of 135±53 SMBG readings over a month. For the following six months, the subjects recorded occurrences of SH. A t-test demonstrated retrospectively that subjects with a history of SH had a significantly higher Low BG Index, 5.2 vs. 2.0, t=4.2, p<0.001, compared to subjects without a history of SH. Prospectively, multiple regression with a leading predictor showed that the Low BG Index accounted for 46% of the variance of SH episodes within the following 6 months. In comparison, the standard variables in the DCCT accounted for only 8% of the variance of future SH.

Measurement of Physiological BG Regulating Parameters:

According to the invention, the physiological BG regulating parameters used to predict near future BG profiles and the onset of hypoglycemia, as well as the BG measurements used to asses the risk of hypoglycemia, can be measured, detected, and/or calculated using any methodology known in the art for accomplishing the desired physiological measurement. Further, the physiological parameters can be recorded to generate the desired data history profiles using any data recording mechanism known in the art which are capable of interfacing with the measurement, detection, and/or calculation device or mechanism. The data recording mechanism can either be an integral component of the measurement, detection, and/or calculation mechanism, or it can be a separate mechanism which allows for the manual or automated input of physiological parameter data.

More particularly, BG levels can be determined by performing routine BG sampling with various known reflectance meters. For instance, see U.S. Pat. Nos. 5,019,974 and 4,731,726 for examples of BG monitoring and recording devices. Contemporary devices provide easy and quick BG assessments and are capable of storing hundreds of BG readings. New sampling technologies are emerging that can perform automatic frequent BG determinations and store the data for future retrieval. Thus, available technology can provide the means for regular BG sampling and can record data for generating BG history profiles.

The insulin infusion/injection history profile can be generated by manual recording and input of insulin injection information, by automated data capture methodologies such as those included in insulin infusion pump, or by any other data acquisition method known in the art. For instance, insulin infusion devices (insulin pumps) can be designed for continuous delivery of insulin and delivery of pre-programmed boluses in conjunction with data acquisition. Thus, the insulin delivery rate is readily available, together with information about the type of insulin (rapid, regular, lente, etc.) that is being used. Alternatively, manual injections of insulin can be performed and a manual recordation of the time, amount, type, etc. can be made.

Physical activity, past and present, can be evaluated through patient-kept diaries or from on-line physiological measurements such as HR. For example, the average HR in the previous hour, compared to this individual's heartbeat during rest, can provide information about the physical activity during that hour. Other measurements might include non-invasive recording of muscle activity.

Counter-regulatory response can be evaluated by monitoring the activation of the sympathetic nervous system. The sympathetic neuro-hormones epinephrine and norepinephrine oppose insulin action and lead to a diminished rate of fall of BG. For example, the degree of sympathetic nervous system activation can be estimated from HRV measurements. In one embodiment, the power spectra of RR time series can be examined for bandwidth-specific variance with the idea that low-frequency power (about 0.02 to 0.2 Hz) arises from sympathetic nervous system activity.

In a particular embodiment of the invention, HR and HRV history profiles can be generated using any EKG apparatus known in the art which is capable of detecting and recording an EKG profile and calculating a power spectra from RR interval time series information.

HR and HRV Parameters:

As shown in FIG. 12, our mathematical model predicting BG fits observed data well. An important component of the model is CR(t) the estimated contribution of counter-regulatory mechanisms. This term is not directly measurable but relates directly to activity of the sympathetic arm of the autonomic nervous system. As described above, measurement of HRV can serve as estimates of CR(t). These HRV-based estimates are denoted as CR(HRV(t-1)) in the bio-mathematical routine described above for the prediction of near future BG profiles.

In one embodiment of the invention, as mentioned above, frequency domain analysis of time series of RR intervals generated by EKG can be used to determine autonomic state. There are three peaks in the HRV power spectrum, at 0.04 Hz, 0.12 Hz, and at the respiratory rate, which are named the low-, mid-, and high-frequency peaks respectively. See Aksefrod, et al., "Power spectrum analysis of heart rate fluctuation: a quantitative probe of beat-to-beat cardiovascular control," *Science* 213: 220–22 (1991).

While not wishing to be bound by theory, it has been shown that atropine, which blocks muscarinic acetylcholine receptors to thereby inhibit the effects of the parasympathetic nervous system, eliminated the high-frequency peak and greatly reduced the mid-frequency peak. Subsequent addition of propranolol, which blocks beta-adrenergic receptors to thereby inhibit the sympathetic nervous system, eliminated the remaining peaks. As such, it is believed that high-frequency power (HF; 0.15 to 0.5 Hz; i.e., respiratory sinus arrhythmia) results mainly from parasympathetic activity, and that low frequency power (LF; 0.05 to 0.15 Hz) results mainly from sympathetic activity.

It has been suggested that frequency domain analysis of HRV can give information on the balance of sympathetic and parasympathetic activity. See Pagani, et al., "Power spectral analysis of heart rate and arterial pressure variabilities as a marker of sympatho-vagal interaction in man and conscious dog," *Circ. Res.* 59: 178–93, 1986. Specifically, it was proposed that the ratio of low-frequency to high-frequency power (LF/HF) gave the "sympatho-vagal balance." Based on these findings, it is believed that the frequency content of RR time series measurements reflects changes in autonomic status rather than estimates the steady-state level. As such, these kinds of non-invasive measures have been used in studying autonomic fluctuation in a variety of disease states.

In other embodiments of the invention, alternative measures for determining HRV that are not predicated on frequency domain analysis to develop relevant parameters can be used to estimate autonomic activity. For instance, sample entropy (SampEn), a measure of regularity and order in a time series may be used. This measure is based on approximate entropy (ApEn), and is the negative logarithm of the probability that two short sequences in a time series that are arbitrarily similar will remain similar. A regular, repeating time series will generate probabilities near 1 with corresponding SampEn values near 0. It is believed that respiratory sinus arrhythmia, the marker of parasympathetic activity, may result in lower SampEn values. One justification for this belief is that a periodic signal, such as a sine wave, results in a SampEn value of 0, while a time series of random numbers has much larger SampEn values.

A potential problem with using HRV as an estimate of counter-regulation involves the detection of changes in autonomic activity in patients whose disease has progressed to such an extent that autonomic reactivity has been diminished. Indeed, reduced HRV is a standard diagnostic indicator of diabetic autonomic neuropathy. As such, the present invention is particularly applicable to patients with T1DM which demonstrate the presence of HF power. The aim of implementing a strategy for early detection of severe hypoglycemia is to allow better glucose control over a long period of time. Therefore, application of the present invention to patients suffering from T1DM can be highly efficient when applied to patients before end-organ damage is present.

In summary, the predetermined bio-mathematical routines for predicting near future BG profiles and for assessing the risk of hypoglycemia can provide tools for quantitative evaluation of the functional relationships between the major variables determining a patient s BG fluctuations. The transformation of the BG scale and the BG Risk Function can provide the numerical space where computations can be carried out. The HR and the HRV can provide additional information about physical activity and autonomic reaction. This integrated approach can ensure that the numerical methods employed according to the invention are not only precise from a functionally mechanistic point of view, but are also sensitive to hypoglycemia.

$P_1$: Principal Process #1; Model process by which consumed food elevates BG.
$P_2$: Principal Process #2; Model process by which injected/infused insulin reduces BG;
$P_2$: Principal Process #3; Model process by which physical activity reduces BG;
CR: Counter-regulatory Process; Model process by which liver stores elevate BG;
Reg: Model process by which BG levels inhibit process CR;
Rep: Replenishment Process; Model process by which BG levels replenish liver stores.
R1: Regulatory Interaction; Model process by which physical activity promotes insulin action.

Figure 3:
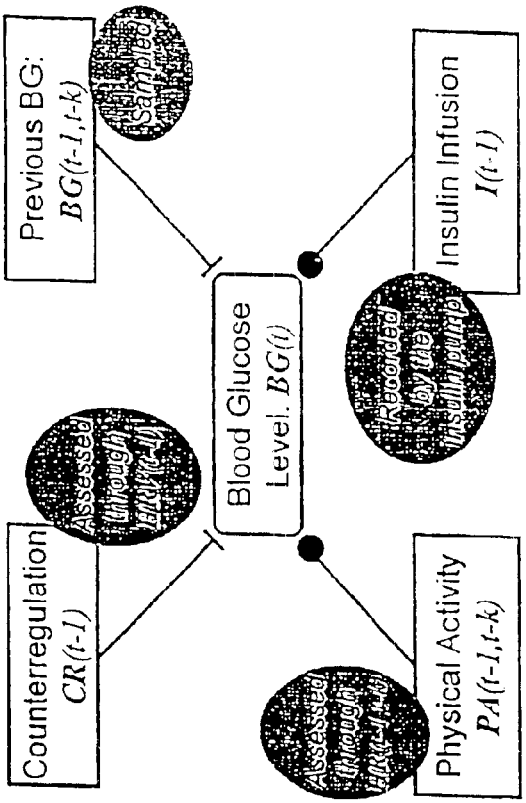

FIG. 3: Dynamic forecast of BG fluctuations: At a future point in time, the BG level depends on the following parameters: 1) current blood glucose level, 2) ongoing insulin infusion, 3) past and current physical activity as evaluated from heart rate, and 4) hormonal counter-regulation as estimated from indicators of sympathetic nervous system activity (heart rate variability).

Figure 4:
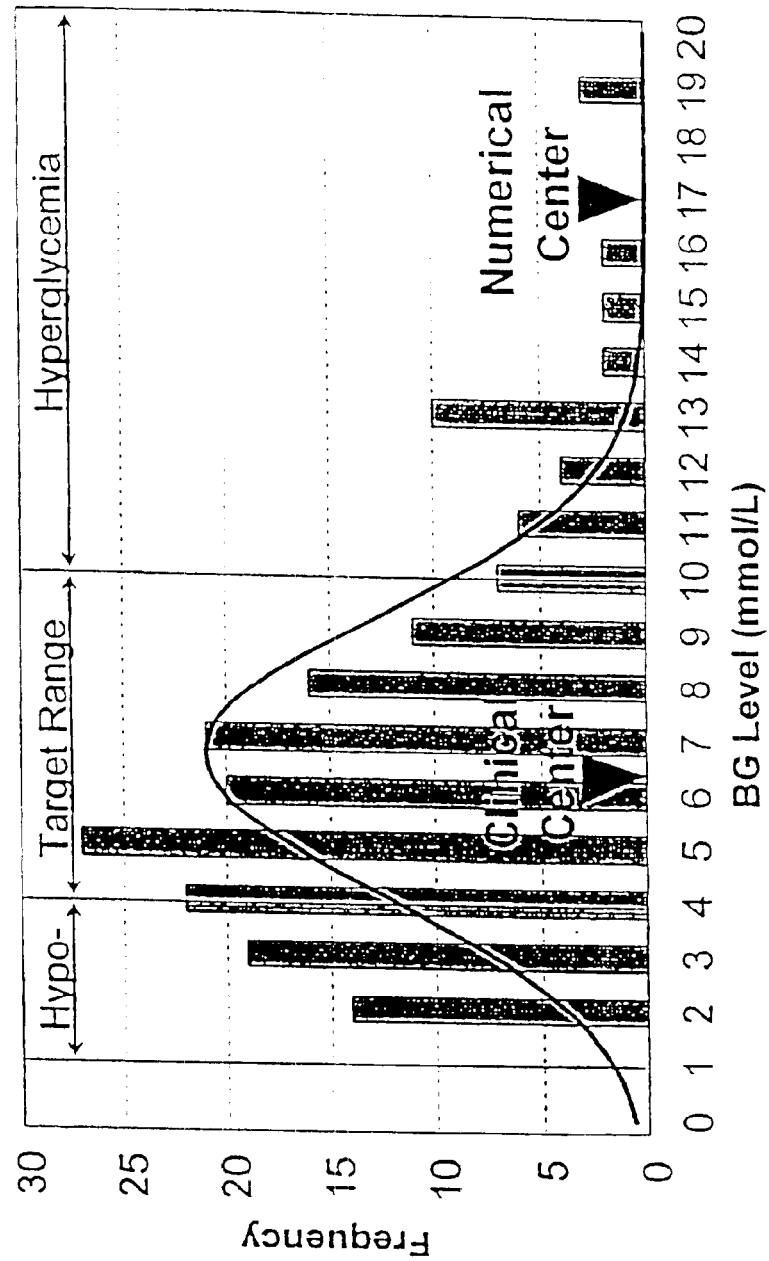

FIG. 4: Typical Distribution of BG Readings: The range of most blood glucose reference meters is 1.1 to 33.3 mmol/L. This scale is not symmetric as hypoglycemia is usually identified as a blood glucose below 3.9 mmol/L and hyperglycemia as blood glucose above 10 mmol/L. This Figure presents this asymmetry by a typical data distribution of 186 readings.

Figure 5:
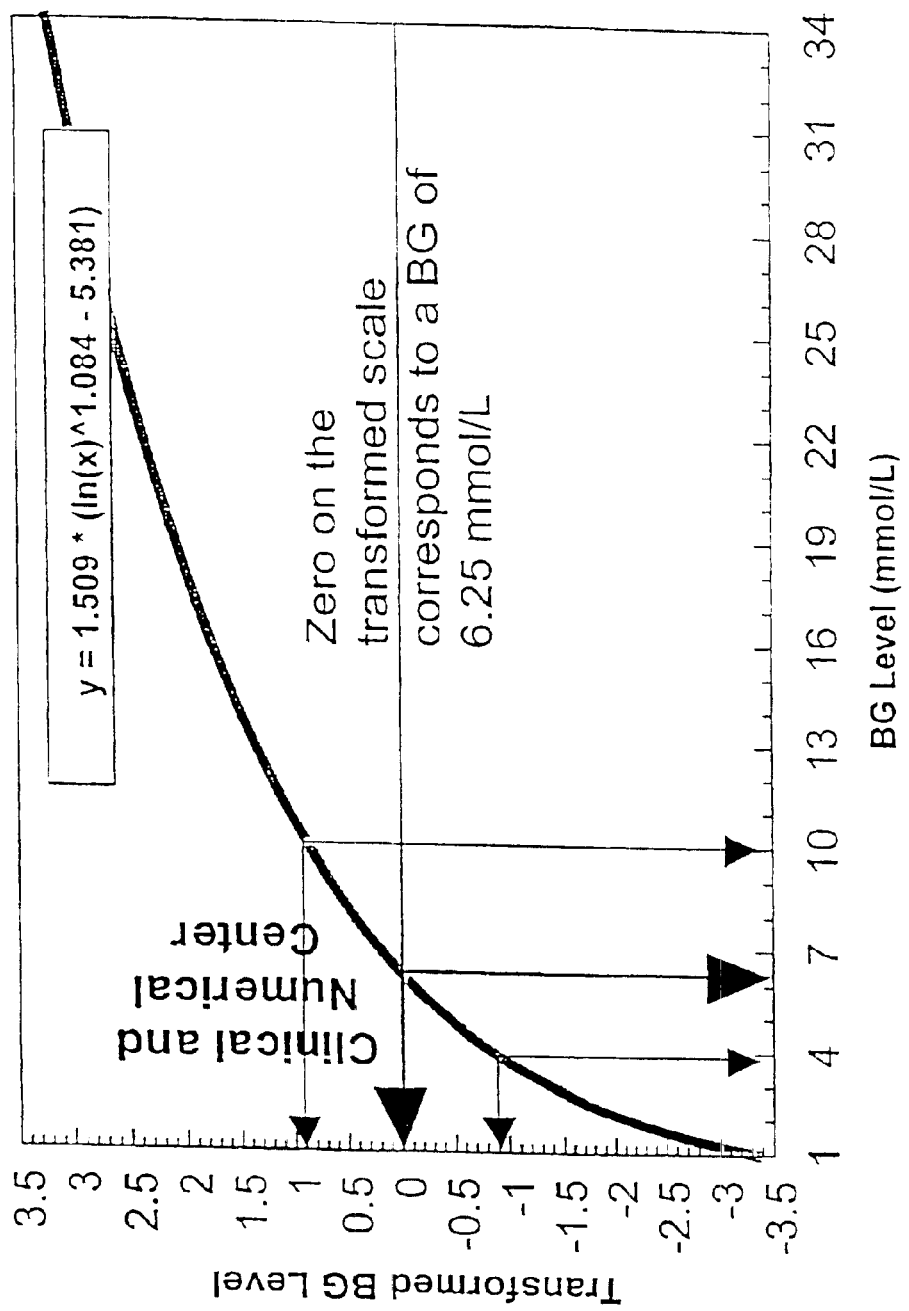

FIG. 5: BG Scale Symmetrization Transformation: This graph illustrates the data transformation in which both the clinical and the numerical center of the scale (FIG. 4) coincide with zero.

Figure 6:
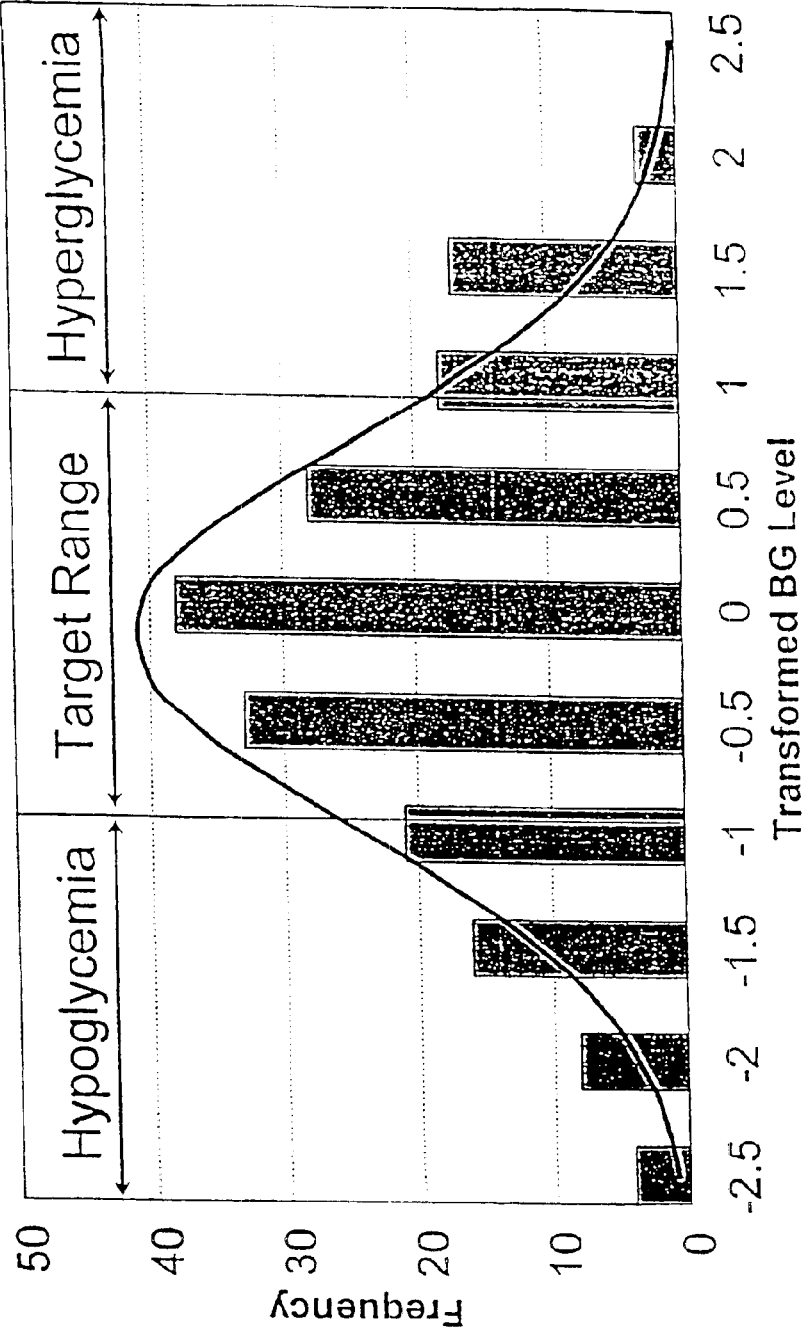

FIG. 6: The Distribution of the Transformed BG Readings: As a result of the data transformation of FIG. 5 the distribution of blood glucose readings of a subject with T1DM becomes symmetric or is statistically normal.

Figure 7:
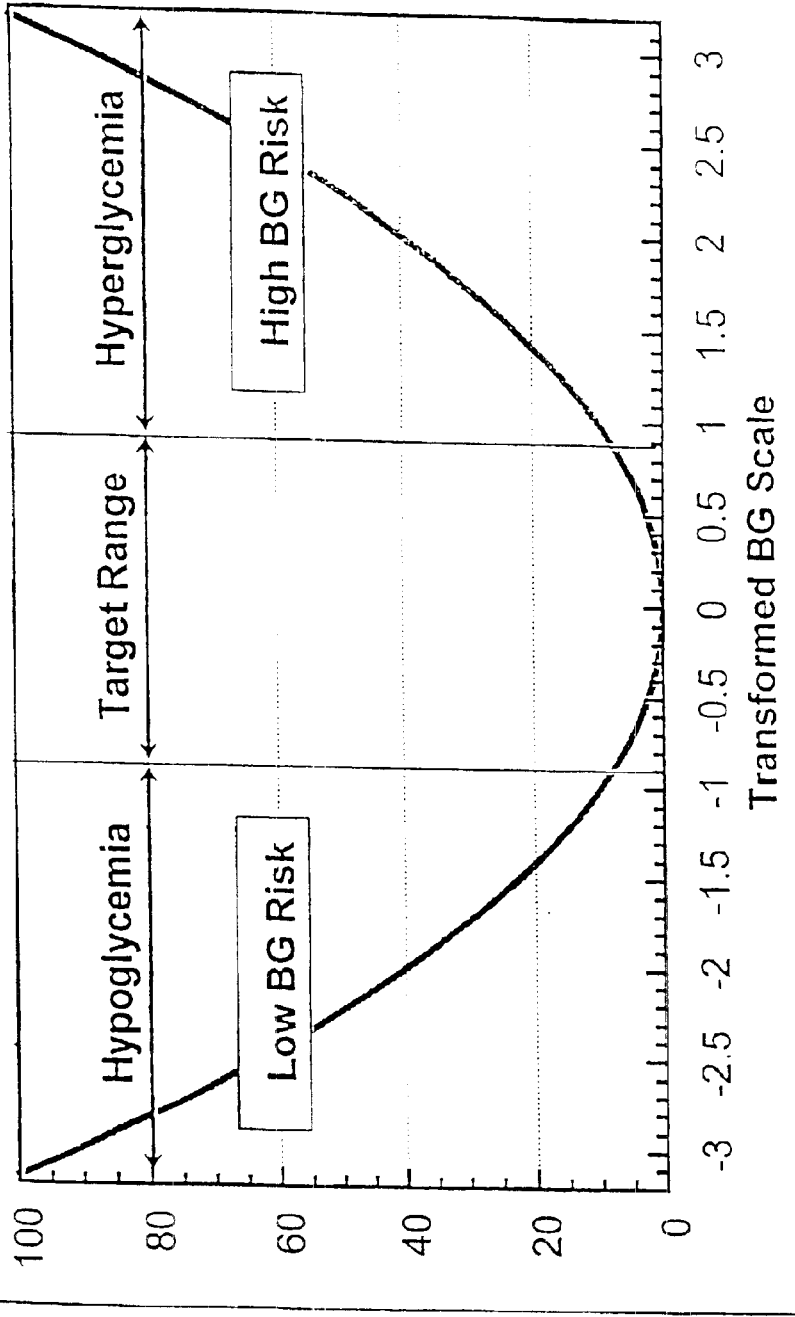

FIG. 7: Defining, the BG Risk Function: This graph presents a quadratic risk function superimposed over the transformed BG scale.

Figure 8:
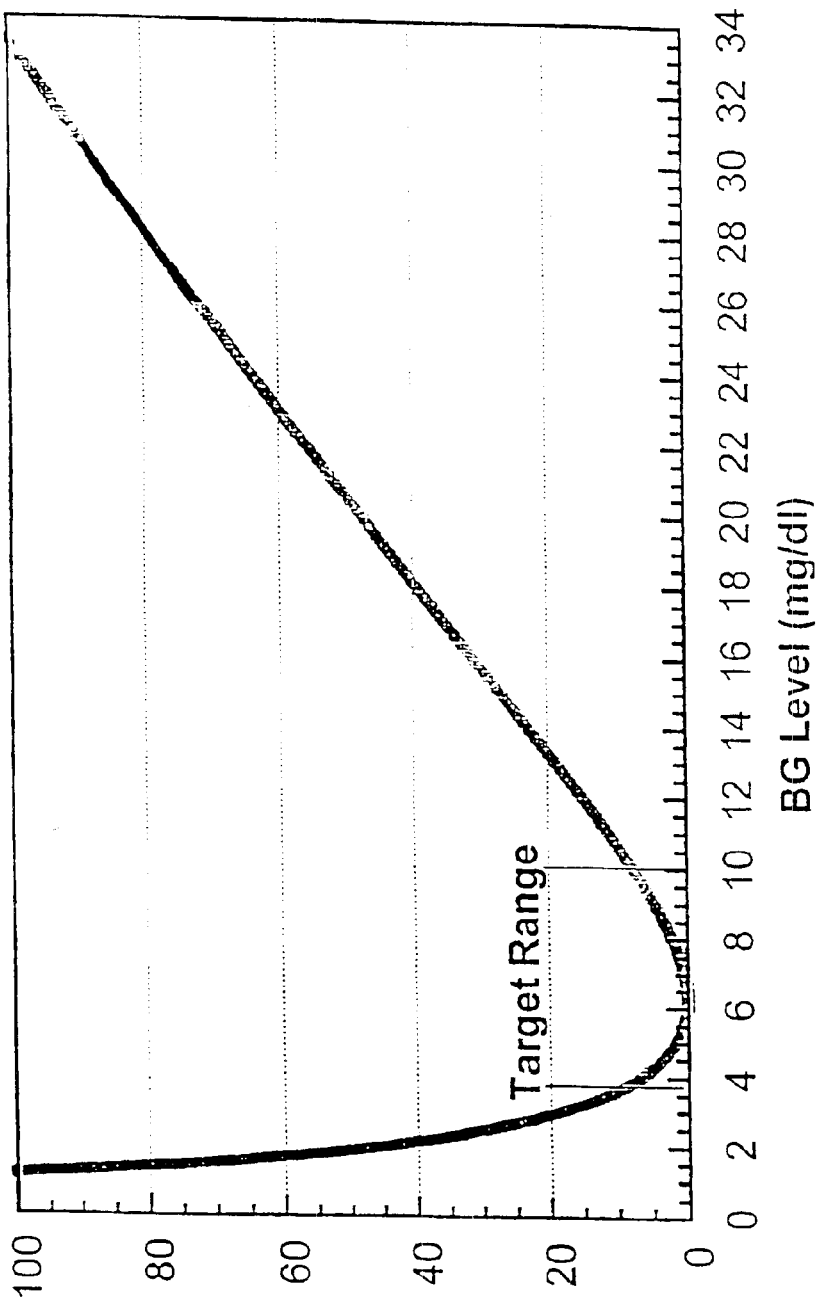

FIG. 8: BG Risk Function (Weighting): This graph presents the BG Risk Function in the original BG scale. The function achieved by presenting the BG Risk Function in the original BG scale provides the weighting of the BG readings that is the basis for computation of the Low and High BG Indices.

Figure 9:
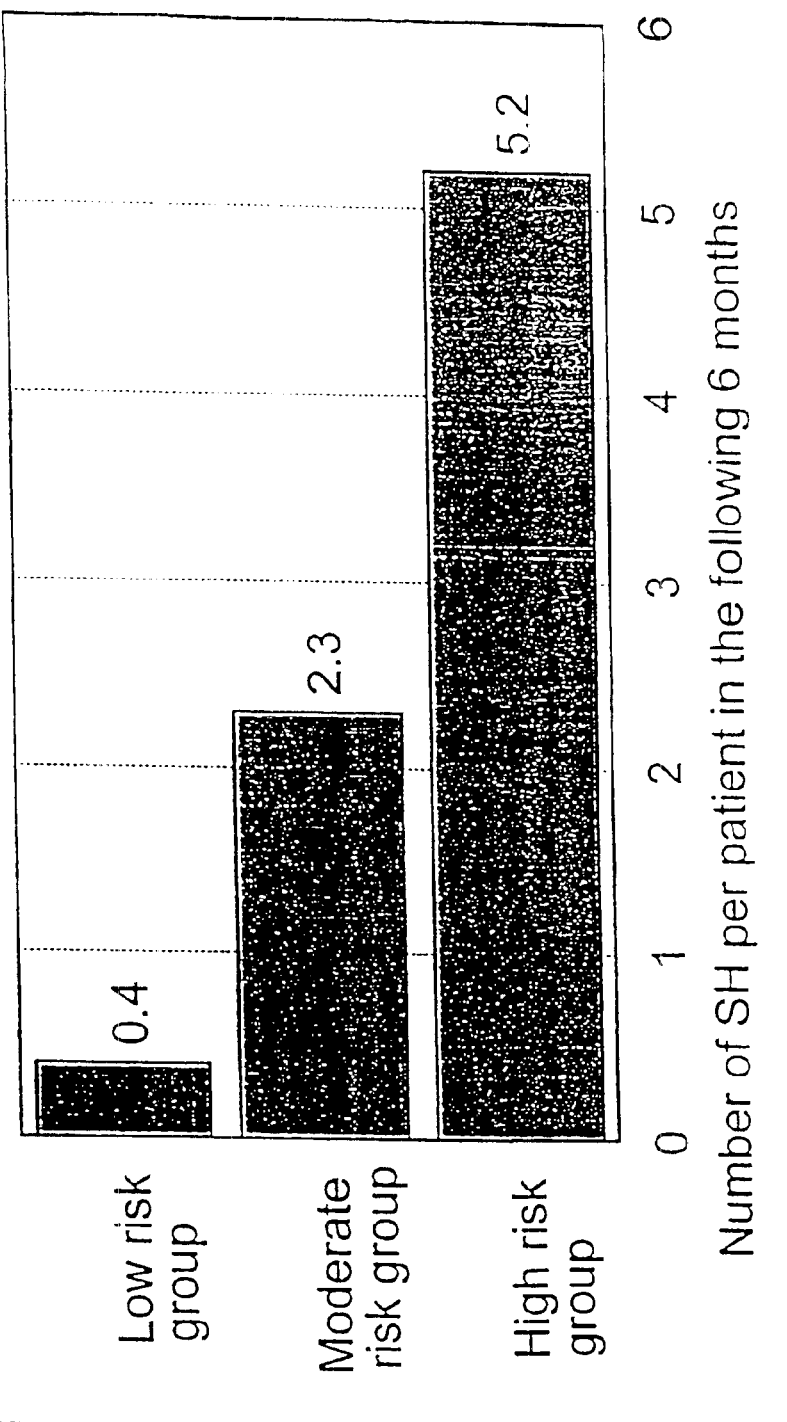

FIG. 9: Risk Groups Identified by the Low BG Index and Number of Future SH Episodes: This Figure shows the accuracy of the classification of the subjects with regard to their risk for severe hypoglycemia, on the basis of one-month of routine SMBG readings.

Figure 10:
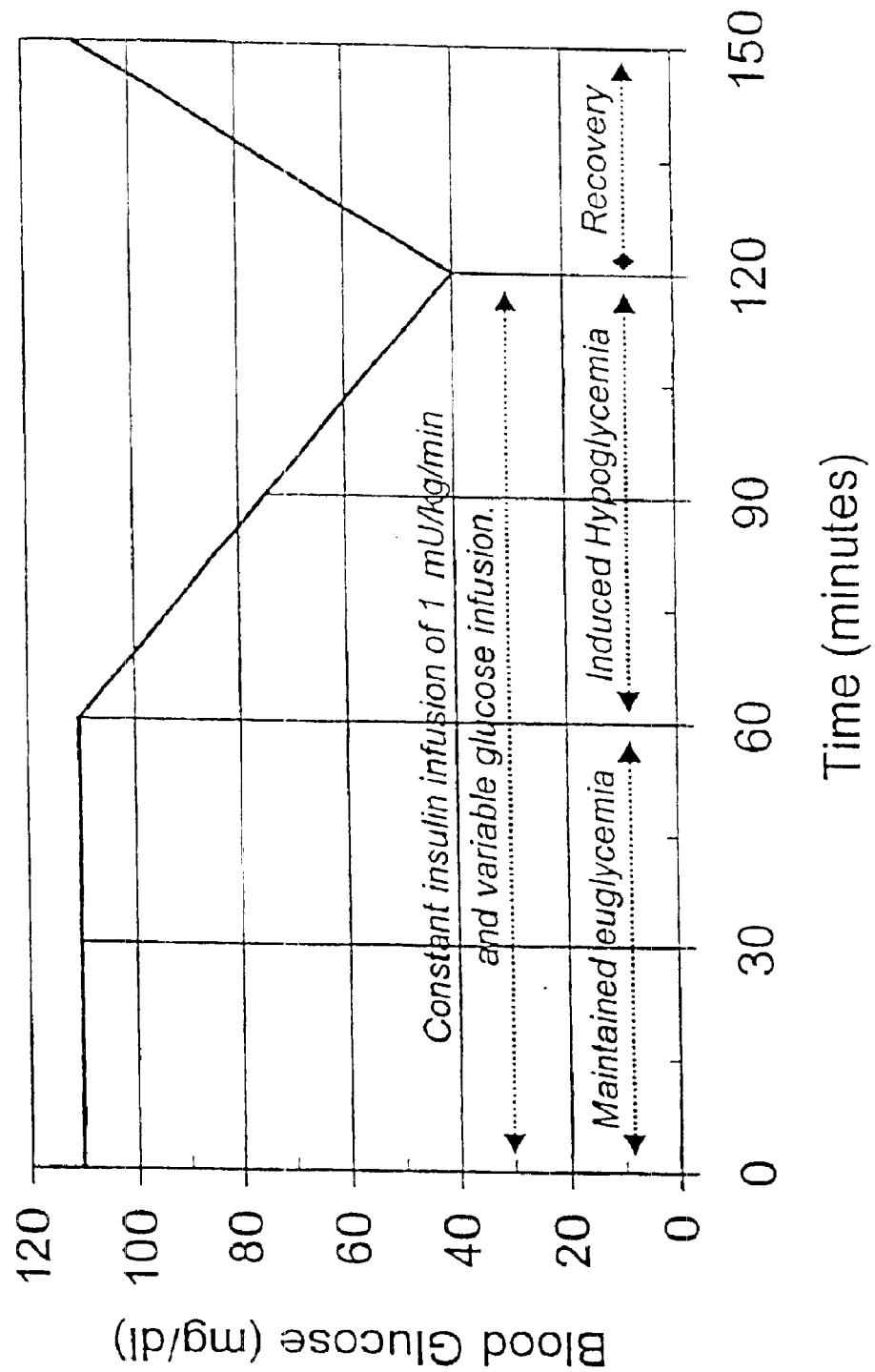

FIG. 10: Hvperinsulinemic Clamp: Design of the Study: This Figure shows the three phases of an experiment undertaken to validate the general dynamic network of FIG. 2. Blood glucose during Phase 1 was maintained at a constant concentration. Then blood glucose was lowered to a target level by varying the dextrose infusion. After hypoglycemia was induced, blood glucose was raised.

FIG. 11: Insulin-Glucose Counter-regulation Network During Controlled Hyperinsulinemic Clamp: This Figure illustrates the simplified version of the network model of FIG. 2 which was used to approximate the insulin-dextrose-blood glucose data sets of 40 subjects in the initial study. There is a continuous insulin infusion at a constant rate and a direct variable dextrose infusion replaces food intake. A counter-regulation loop (CR(t)–Reg(t)) is anticipated at lower BG levels.

FIG. 12: Counter-regulation: This Figure illustrates how the mathematical model predicting blood glucose fits the observed data Counter-regulation is not directly measurable but relates directly to the activity of the sympathetic arm of the autonomic nervous system. Here the model onset of counter-regulation was validated by the rise in epinephrine concentration.

FIG. 13: Multi-component Counter-regulatory Response to Low BG: This Figure illustrates the data, model fit, and the predicted counter-regulatory response of a subject exhibiting bi-modal counter-regulation. The left y-axis (BG (mmol/L)) refers to two variables: the BG data plotted by circles and the model fit. The dextrose infusion data and the predicted counter-regulation rate are plotted along the right y-axis. The Figure includes the coefficient of determination, $R^2$, of the nonlinear fit.

FIG. 14: Design of Hospital Laboratory Study: This Figure illustrates the target blood glucose levels during a laboratory study. During the first hour (euglycemia), BG will be maintained between 5.5 and 8 mmol/L through a continuous insulin infusion of 1 mU/kg/min and a variable infusion of 20% dextrose solution. During the second hour (progressive hypoglycemia), insulin infusion will continue and dextrose infusion will be discontinued (or sufficiently reduced) to ensure a steady BG fall of 0.6 mmol/L/10 min for 60 min, with a target BG level between 2.2 and 2.5 mmol/L.

MODE FOR CARRYING OUT THE INVENTION

EXAMPLE 1

Figure 1:
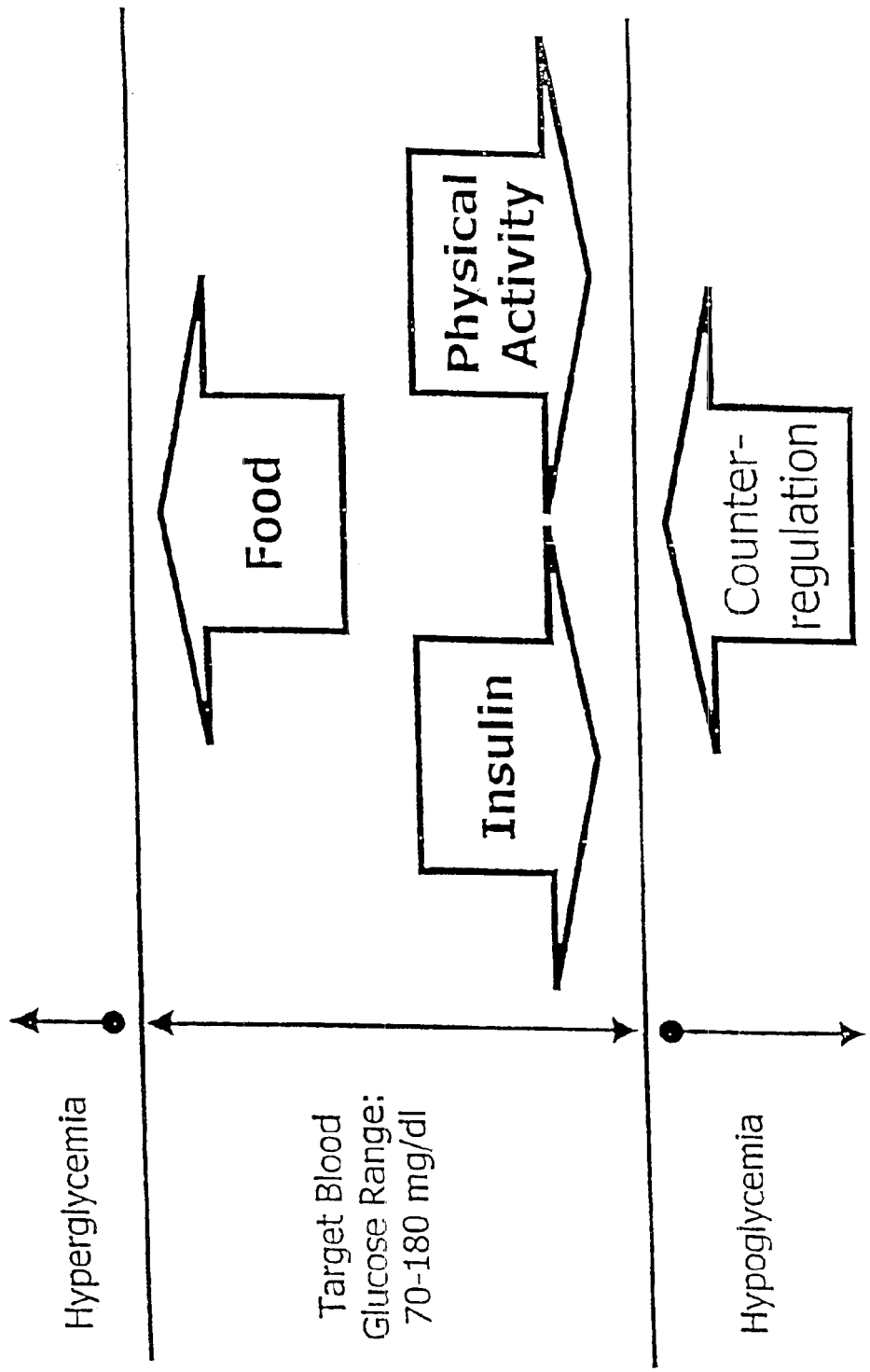
FIG. 1: Major factors determining BG dynamics: BG level fluctuations of a person with T1DM depend on the temporal patterning of at least four major factors: food intake, insulin injection/infusion, physical activity and glucose counter-regulation.
Figure 2:
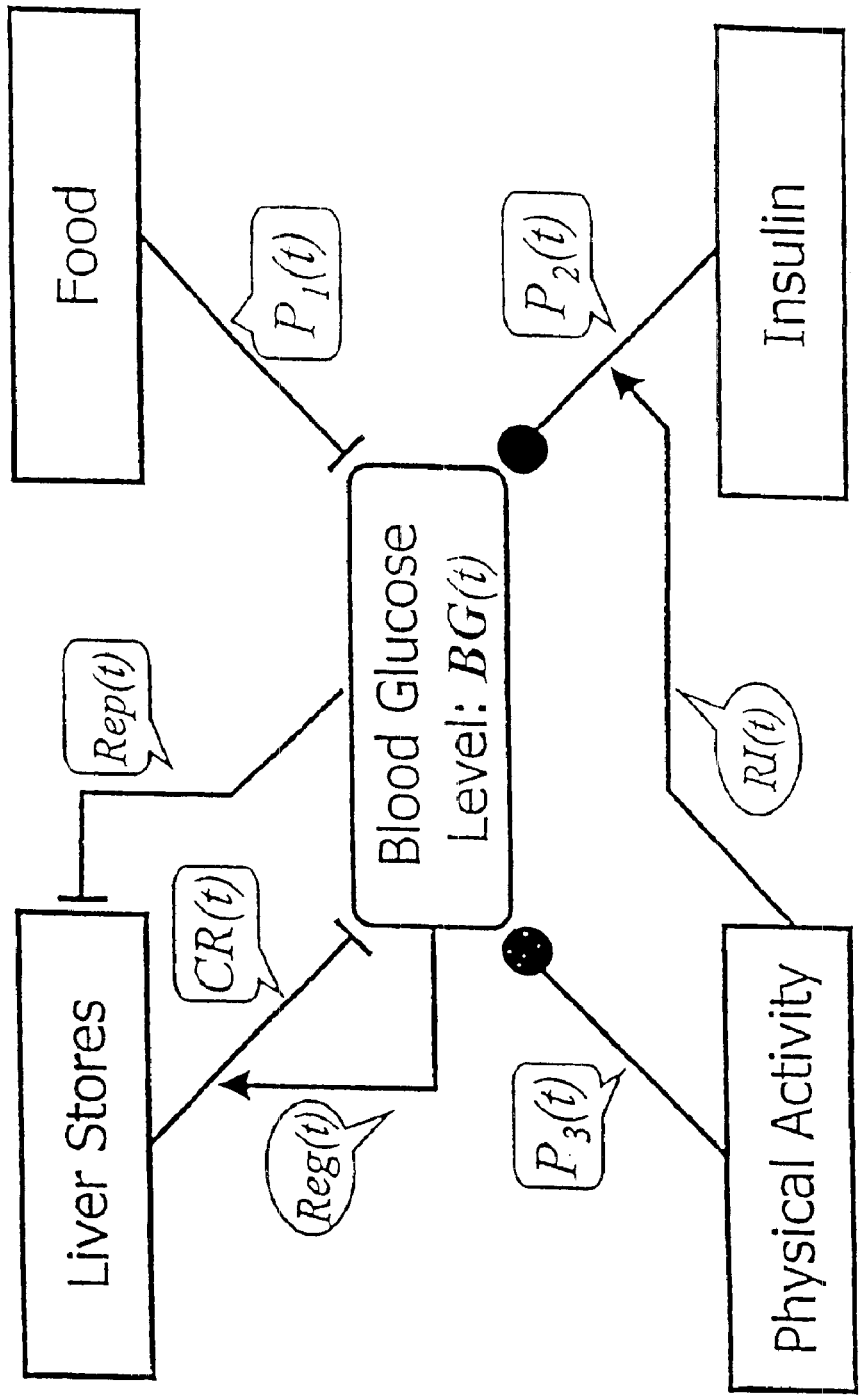
FIG. 2: Dynamic network model of BG fluctuations: The interaction of the major factors responsible for temporal BG fluctuations translates into a dynamic network of behavioral and physiologic time dependent processes.

Dynamic Network Model of BG Fluctuations During Controlled Hyperinsulinemic Clamp As a first step to the validation of the general dynamic network presented in FIG. 2, the following laboratory study was conducted. Forty subjects suffering from T1DM for at least two years and taking insulin since the time of diagnosis were admitted to the University of Virginia Central Clinical Research Center. There were 16 males and 24 females, with mean age 35.5 years (SD=8.1), mean duration of disease 16.9 years (SD=9.6), mean insulin units/day 42.0 (SD=15.5), and mean glycosylated hemoglobin 8.5% (SD=1.7).

During the night before the study, BG was maintained between 5.6–8.3 mmol/L, with intravenous regular human insulin as per a previously published insulin infusion protocol. See Bolli, et al., "A reliable and reproducible test for adequate glucose counter-regulation in type 1 diabetes mellitus," *Diabetes* 33: 732–37 (1984). Subjects were given dinner and a bedtime snack the evening before the study, but remained fasting on the morning of the study. No caffeinated beverages were consumed after hospital admission. On the morning of the study, IVs were placed in the nondominant forearm. Insulin was continuously infused at a constant rate of 1.0 mU/kg/min and a 20% dextrose solution was infused at a variable rate to maintain BG at 5.6 mmol/L.

During Phase 1 (euglycemia), BG was maintained between 5.6 and 8.3 mmol/L. During Phase 2 (BG reduction), BG was steadily lowered to a target level of 2.2 mmol/L by varying the dextrose infusion. Arterialized blood (achieved by warming the hand in a heated glove to 50° C.) was sampled for glucose concentration every 5 minutes and for plasma epinephrine concentration every 10 minutes (see FIG. 10).

A simplified version of the network model in FIG. 2 was used to approximate the insulin-dextrose-BG data sets of the 40 subjects. FIG. 11 presents this simplified network of interactions. During this test, the influence of the subjects' physical activity is negligible and the replenishment process of liver glucose stores can be ignored because of the induced hyperinsulinemia. Instead of insulin injections, there is continuous insulin infusion (process I) at a constant rate, and direct variable dextrose infusion (process G(t)) replaces food intake. A counter-regulation loop (CR(t)–Reg(t)) is anticipated at lower BG levels.

It was assumed that dextrose infusion influenced BG positively through an unknown dextrose conversion parameter, and that the rate of BG decay was inversely proportional to BG level, through an unknown insulin utilization parameter. During Phase 1 (euglycemia), no counter-regulatory response was anticipated, while during Phase 2 (descent into hypoglycemia), this response was modeled through a parameterized counter-regulation function. An adaptive sliding algorithm and special software program were designed to evaluate the parameters of the system for each individual subject. The program was designed to automatically detect onset of counter-regulation and evaluate the rate and amount of each individual's counter-regulatory response, if one was present. The nonlinear fits were extremely good. The average coefficient of determination across subjects was 96.6% (SD=3.1), with a maximum of 99.7% and a minimum of 86.5%; seven subjects had coefficients of determination above 99%, while only 2 subjects had coefficients of determination below 90%. Thus, on average, our model explained 96.6% of the variance of subjects' BG fluctuations.

This precise approximation of subjects' BG dynamics resulted in a precise evaluation of their counter-regulatory responses. The rate of counter-regulation of each subject was estimated in units equivalent to mg/kg/min dextrose infusion. Our model indicated that three subjects did not counter-regulate, while three other subjects had statistically non-significant counter-regulatory responses. These estimates were externally validated by subsequently correlating the model-predicted counter-regulation with the measured epinephrine response of the subjects (FIG. 12). For all subjects, their model-predicted counter-regulatory responses were significantly correlated with measured plasma epinephrine concentrations, with more than half of the correlation coefficients above 0.8. This research suggested two previously unrecognized possibilities:

1) Subjects with a history of multiple severe hypoglycemic episodes had slower onset of counter-regulation (p=0.03) compared to subjects with no such history, but not a smaller overall counter-regulation volume. This result clarifies one dimension of the "impaired glucose counter-regulation" associated with risk for hypoglycemia.

2) Glucose counter-regulation may be a multicomponent process: 23 out of the 34 subjects who did counter-regulate at low BG had a bi-modal counter-regulation function with two consecutive peaks at decreasing BG levels (see FIG. 13).

In summary, the demonstrated ability of this model to reliably describe the dynamics of BG fluctuations in both euglycemia and during descent into hypoglycemia, with subsequent initiation of counter-regulation is the basis of the detailed predetermined bio-mathematical routine and information-processing technology for the prediction of near future BG profiles and for the prediction of the onset of hypoglycemia disclosed herein.

EXAMPLE 2

Clinical Validation of the Forecast of Hypoglycemia

A clinical study can be performed, with the following procedure, to further validate the forecast of hypoglycemia. In such a study, twenty subjects will be recruited who meet the following inclusion criteria: having T1DM, taking insulin since the time of diagnosis, and routinely performing SMBG with a meter more than twice daily. All participants will be using insulin pumps to control their diabetes, their age will be between 18 and 30 years, and their $HbA_{1c}$, will be below 90/o. Subjects with obvious autonomic neuropathy (i.e., absence of RSA as defined below) will be excluded, as the relationship between their HRV and low BG may not be useful in the predetermined bio-mathematical routines of the invention. Subjects between 18 and 30 years of age will be selected since they are adults who presumably have a relatively short diabetes duration and relatively low likelihood of cardiac, renal, neurological, or kidney complications. In addition, subjects whose $HbA_{1c}$ levels are at least as low as the conventional controlled subjects in the DCCT will be chosen in order to allow for observation of occasional low BG levels. Subjects should be using ian insulin infusion pump to enable accurate quantification of their insulin infusion.

Subjects will be given a thorough physical examination, including an assessment for autonomic neuropathy and determination of their $HbA_{1c}$. The initial screening should preferable involve at least 35 subjects in order to select 25 of whom will meet the inclusion criteria. The subjects who meet the inclusion criteria will be scheduled for Hospital and Field Study. It is anticipated that 20 subjects will successfully complete both phases collecting reliable, artifact-free data. It is assumed that the data of 5 subjects will be either rejected or these subjects will dropout of the study during, or after, Phase 1.

To ensure that subjects' BG levels are not in a low BG range for 72 hours prior to the study, 3 steps will be taken: Subjects' insulin pumps will be recalibrated to avoid hypoglycemia; subjects will be instructed to eat prophylactically 10 g of glucose whenever their BG is below 5.5 mmol/L; and subjects will be required to test their BG 5 times a day (1 hr. before each meal, at bedtime, and 4 hrs into their sleep). If low BG occurs, hospitalization will be rescheduled.

Phase 1: Laboratory Study

During the evening before the study, subjects will be hospitalized. BG will be maintained overnight between 5.5–8 mmol/L by controlling subjects' insulin pump and frequent BG monitoring. Subjects will not be given caffeine the evening before or the morning of the testing. On the morning of testing, IV's will be placed in subjects' nondominant forearm. During the first hour (euglycemia), BG will be maintained between 5.5 and 8 mmol/L through a continuous insulin infusion of 1 mU/kg/min and a variable infusion of 20% dextrose solution. During the second hour (progressive hypoglycemia), insulin infusion will continue and dextrose infusion will be discontinued (or sufficiently reduced) to ensure a steady BG fall of 0.6 mmol/L/10 min for 60 min. with a target BG level between 2.2 and 2.5 mmol/L (FIG. 14). The protocol will be discontinued if strong expressions of hypoglycemia occur, e.g., lethargy, confusion, disorientation, or inappropriate behavior. During the third hour (recovery), insulin infusion will be discontinued and variable dextrose infusion will be resumed.

Throughout the study, blood will be sampled for glucose concentration every 5 minutes. Arterialized blood will be achieved by warming the hand in a heated glove to 50° C. Every 10 minutes, subjects will rate, on a scale from 0 (None) to 6 (Extreme), the degree to which they are experiencing three of the most common autonomic symptoms (trembling, pounding heart, sweating) and three of the most common neuroglycopenic symptoms (difficulty concentrating, incoordination, lightheaded/dizzy). Counter-regulatory response will be evaluated from BG levels and dextrose and insulin infusion data using a predetermined algorithm. See Kovatchev, et al., "Dynamic network model of glucose counter-regulation in subjects with insulin-requiring diabetes," *Methods in Enzymology*, vol. 321: *Numerical Computer Methods, Part C*, (Michael Johnson and Ludvig Brand, Eds.) Academic Press, New York (in press); Kovatchev, et al., "Modeling insulin-glucose dynamics during insulin induced hypoglycemia, Evaluation of glucose counter-regulation," *J of Theoretical Medicine* 1: 313–23 (1999). These estimates will be correlated with HRV. It is hypothesized that symptoms of hypoglycemia will occur at lower BG levels than will changes in HRV.

EKG recordings will he made using an EKG pre-amplifier (Marquette) and novel HRV measurement system, consisting of an 80486-based microcomputer with a National Instruments AT2200 digital signal processing and analog/digital converter board and custom software for QRS detection and analysis of RR interval time series. The QRS detection scheme has been previously validated and is based on amplitude and duration criteria in a high-pass filtered signal digitized at 4 kHz (resolution 0.25 msec). RR interval time series will be converted to an evenly sampled signal using the method of Berger (Berger, et al., "An efficient algorithm for spectral analysis of heart rate variability," *IEEE Trans. Biomed Eng.* BME 33: 900–4 (1986)), and power spectra will be calculated after detrending and windowing (Press, et al., "Numerical Recipes in FORTRAN," *The Art of Scientific Computing*, Cambridge University Press, New York (1994)).

To control for the variability of HF power as a function of respiratory rate, patients will he instructed to breath in unison with a metronome at 12–15/min (0.2 to 0.25 Hz). See Brown, et al. "Important influence of respiration on human R—R interval power spectra is largely ignored," *J. Appl. Physiol.* 75: 2310–17 (1993). HF power will he calculated by integrating the power spectrum under the respiratory peak ±0.05 Hz. The recording time will he at least 1024 sec, allowing for time series of heart rate that are 4096 points long. Each spectrum will he the average of 7 spectra of windows of 1024 points overlapping by 50%. This procedure reduces the error of spectral estimates by a factor of $1/\sqrt{7}$. See Bendat & Piersol, "*Random data, Analysis and measurement procedures*," John Wiley, New York (1986).

As shown above, the respiratory peak is unambiguous and easily allows quantification by integrating a 0.1 Hz band centered on the respiratory frequency. For portions of the study, subjects will breath in unison with a metronome at 0.2 to 0.25 Hz. An initial screening evaluation of the presence of HF power will he made for each patient and preference will be given to patients with large HF components (e.g., area greater than $10^{-3}$ msec$^2$).

For phase 1 of this study, recordings will be made in the same way for offline analysis. Power spectra and HF power will be calculated every 60 seconds for a sliding window of the previous 1024 seconds. While it is hypothesized that a reduction in HF power will come before symptomatic hypoglycemia, other forms of time series analysis, including SampEn and the power from 0.02 to 0.2 Hz, which is believed to be due to activity of the sympathetic nervous system, will be evaluated. See Richman J S, Moorman J R., "Physiological time-series analysis using approximate entropy and sample entropy", *Amer. J. of Physiology*, 278: H2039–2049 (2000). Candidate HRV measures will be used as input for the mathematical model to predict BG. A screening test of such parameters indicates that a time series of the parameter value should follow the course of the counter-regulatory term in FIG. 6.

Phase 2: Field Study

Approximately a week after the laboratory phase of the study, the participants will enter the second phase—a field assessment of the predetermined bio-mathematical routines of the invention. The Field Study is intended to test whether controlled laboratory findings generalize to subjects' daily routines, in terms of relationships between BG fluctuations and insulin/heart rate/physical activity data. The individual subjects' parameters determined during Phase I will be included in the model of Phase II. The differences will be in the measurement of the major model components and in the greater variability, and therefore greater influence, of subjects' physical activity on their BG fluctuations. This phase will continue one week and will include the following parallel data collections:

1) The subjects will continue using their insulin pumps and will record in diaries the basal rate of insulin infusion, the time and amount of insulin boluses, and the type of insulin used.

2) The subjects will be equipped with interstitial tissue BG monitoring devices (in development by Roche Diagnostics) that will provide continuous BG monitoring. Alternatively, subjects will be required to perform frequent SMBG with a standard memory meter (Accu-check from Roche Diagnostics) 5–7 times a day and will be asked to measure BG whenever they think they experience hypoglycemia, or hyperglycemia.

3) Cardiovascular data will be collected in two ways. First, conventional means for acquisition of EKG and blood pressure data will be used. Continuous EKG will be obtained from Holter recordings using a dedicated recorder. The Heart Center Holter laboratory will read the recorded data and output text files of time stamped RR interval time series. Frequent BP recordings will be made using an ambulatory BP recording system also available through the Heart Center laboratory. The novel FORTRAN and C++ programs discussed above will be used for offline analysis of RR interval time series and BP time series, and new software programs will be developed as necessary. Second, a prototypical device engineered by Empirical Technologies for non-invasive recording of heart rate, respiratory rate, and changes in blood pressure will be used.

4) Physical activity date will be recorded by wrist-worn actigraphs (from Ambulatory Monitoring, Inc., Ardsley, N.Y., catalog number 21.000 and actigraph field interface unit with ACT software, catalog number 21.185).

Data Analysis

For each subject's individual data, the goodness-of-fit of the predetermined bio-mathematical routines according to the invention will be evaluated based on hospital laboratory data. Since the model is intrinsically non-linear, standard ANOVA with its usual F-statistic and significance level cannot be computed. Thus, the accuracy of the data fit will be tested by the coefficient of determination, usually interpreted as the percentage of the total variation of the dependent variable around its mean that is explained by the fitted model. See Kvalseth, "Cautionary note about R squared," *The American Statistician* 39: 279–85 (1985). The goodness-of-fit of each model will be evaluated by the closeness of its coefficient of determination to 100%. A very good model fit and high coefficients of determination, essentially above 95% is expected. Once the parameters of the model are available from hospital data, field data will be used to evaluate the bio-mathematical routines ability for on-line prediction of hypoglycemia. With these data, it is expected that the bio-mathematical routines of the invention will be able to explain correctly over 50% of the total variation in BG fluctuations of each subject. In addition, it is expected that the bio-mathematical routines of the invention will predict 90% of the low BG episodes of a subject about an hour before their occurrence.

INDUSTRIAL APPLICABILITY

The invention is applicable to the evaluation and treatment of patients with Insulin Dependent Diabetes. The invention allows for less frequent, and therefore less invasive, uninterrupted monitoring of blood glucose levels and an evaluation of the risk of hypoglycemia.

The embodiments described herein-above are merely illustrative and are not intended to limit the scope of the invention. It is understood that various changes, alterations, rearrangements and modification can be made by those skilled in the art without departing from the spirit and scope of the present invention.

What is claimed is:

1. A method for predicting a near future BG profile and the onset of hypoglycemia comprising the steps of:

monitoring and recording a BG history profile;

monitoring and recording an insulin infusion and/or injection history profile;

monitoring and recording a HR history profile as an estimate of physical activity;

monitoring and recording a HRV history profile as an estimate of sympathetic nervous system activity;

determining a predicted near future BG profile using a first predetermined bio-mathematical routine; and evaluating the near future BG profile to predict the onset of hypoglycemia in the near future based on an assessed risk of hypoglycemia, wherein the assessed risk of hypoglycemia is determined using a second predetermined bio-mathematical routine using a computerized processor.

2. The method of claim 1 further including the step of adjusting insulin infusion and/or injection rates based on the predicted near future BG profile and the predicted onset of hypoglycemia.

3. The method of claim 1 wherein the step of monitoring and recording HRV history profiles further includes the step of using an EKG to measure and evaluate the power spectra of RR time series as an estimate of HRV.

4. The method of claim 1 wherein the second predetermined bio-mathematical routine assesses the risk of hypoglycemia based on a Low BG Index which is determined using a BG Risk Function.

5. The method of claim 1 wherein the second predetermined bio-mathematical routine comprises the steps of:

receiving and recording a BG history profile;

transforming the BG history profile scale to obtain a symmetrical distribution scale;

introducing a BG Risk Function to obtain a Low BG Index; and determining the assessed risk of hypoglycemia based on the Low BG Index.

6. A method for predicting a near future BG profile and the onset of hypoglycemia in the near future comprising the steps of:

receiving data input regarding BG history, insulin infusion/injection history, HR history, and HRV history;

evaluating the data input received using a first predetermined bio-mathematical routine to predict a near future BG profile; and evaluating the near future BG profile to predict the onset of hypoglycemia in the near future based on an assessed risk of hypoglycemia, wherein the assessed risk of hypoglycemia is determined using a second predetermined bio-mathematical routine using a computerized processor.

7. The method of claim 6 wherein the second predetermined bio-mathematical routine assesses the risk of hypoglycemia based on a Low BG Index which is determined using a BG Risk Function.

8. The method of claim 6 wherein the second predetermined bio-mathematical routine comprises the steps of:

transforming the BG history profile scale to obtain a symmetrical distribution scale;

introducing a BG Risk Function to obtain a Low BG Index; and determining the assessed risk of hypoglycemia based on the Low BG Index.

9. An apparatus for predicting a near future BG profile and the onset of hypoglycemia comprising:

a BG history profile recording mechanism;

an insulin infusion and/or injection history profile recording mechanism;

a HR history profile recording mechanism;

a HRV history profile recording mechanism;

a near future BG profile prediction module for predicting the near future BG profile using a first predetermined bio-mathematical routine; and a hypoglycemia prediction module for predicting the onset of hypoglycemia based on an assessed risk of hypoglycemia, wherein the assessed risk of hypoglycemia is determined by a computer processor using a second predetermined bio-mathematical routine.

10. The apparatus of claim 9 further comprising an BG monitoring module associated with the BG history profile recording mechanism.

11. The apparatus of claim 9 further comprising an HRV determination module associated with the HRV history profile recording module, wherein the HRV determination module comprises an EKG which evaluates the power spectra of RR time series as an estimate of HRV.

12. The apparatus of claim 9 further comprising an insulin infusion module associated with the insulin infusion and/or injection history profile recording module, and an insulin-regulation module which adjusts insulin infusion based on the predicted near future BG profile and the predicted onset of hypoglycemia.

13. The apparatus of claim 9 further comprising a hypoglycemia risk assessment module which determines the assessed risk of hypoglycemia using the second predetermined bio-mathematical routine.

14. The apparatus of claim 13 wherein the hypoglycemia risk assessment module comprises:

an interface for receiving data regarding a BG history profile;

a scale transformation module for transforming the BG history profile scale to obtain a symmetrical distribution scale;

a BG Risk Function module for determining a Low BG Index; and a hypoglycemia risk classification module for determining the assessed risk of hypoglycemia based on the Low BG Index.

15. An apparatus for predicting a near future BG profile and the onset of hypoglycemia comprising:

an interface for receiving data regarding BG history, insulin infusion and/or injection history, HR history, and HRV history profiles;

a BG prediction module for predicting a near future BG profile using a first predetermined bio-mathematical routine; and a hypoglycemia prediction module for predicting the onset of hypoglycemia in the near future based on an assessed risk of hypoglycemia, wherein the assessed risk of hypoglycemia is determined by a computer processor using a second predetermined bio-mathematical routine.

16. The apparatus of claim 15 further including a hypoglycemia risk assessment module for determining the assessed risk of hypoglycemia using the second predetermined bio-mathematical routine.

* * * * *